US009956291B2

(12) United States Patent
Mousa

(10) Patent No.: US 9,956,291 B2
(45) Date of Patent: May 1, 2018

(54) NANOFORMULATION AND METHODS OF USE OF THYROID RECEPTOR BETA1 AGONISTS FOR LIVER TARGETING

(71) Applicant: Shaker A. Mousa, Wynantskill, NY (US)

(72) Inventor: Shaker A. Mousa, Wynantskill, NY (US)

(*) Notice: Subject to any disclaimer, the term of this patent is extended or adjusted under 35 U.S.C. 154(b) by 703 days.

(21) Appl. No.: 13/938,308

(22) Filed: Jul. 10, 2013

(65) Prior Publication Data
US 2014/0017329 A1  Jan. 16, 2014

Related U.S. Application Data

(60) Provisional application No. 61/669,725, filed on Jul. 10, 2012.

(51) Int. Cl.
| | | |
|---|---|---|
| *A61K 47/26* | (2006.01) |
| *A61K 47/12* | (2006.01) |
| *A61K 31/455* | (2006.01) |
| *A61K 31/197* | (2006.01) |
| *A61K 31/192* | (2006.01) |
| *A61K 45/06* | (2006.01) |
| *A61K 31/19* | (2006.01) |
| *A61K 31/198* | (2006.01) |
| *A61K 31/7032* | (2006.01) |
| *A61K 49/00* | (2006.01) |
| *A61K 47/54* | (2017.01) |
| *A61K 47/69* | (2017.01) |

(52) U.S. Cl.
CPC .............. *A61K 47/26* (2013.01); *A61K 31/19* (2013.01); *A61K 31/198* (2013.01); *A61K 31/7032* (2013.01); *A61K 45/06* (2013.01); *A61K 47/542* (2017.08); *A61K 47/6937* (2017.08); *A61K 47/6939* (2017.08); *A61K 49/0093* (2013.01)

(58) Field of Classification Search
None
See application file for complete search history.

(56) References Cited

U.S. PATENT DOCUMENTS

| 2004/0166158 | A1* | 8/2004 | Davis ................... A61K 9/1652 424/468 |
| 2005/0118252 | A1* | 6/2005 | Bae ...................... A61K 9/1075 424/450 |
| 2008/0200948 | A1* | 8/2008 | Utecht ................. A61K 9/0048 606/214 |
| 2008/0220055 | A1* | 9/2008 | Ludwig ................... B82Y 5/00 424/450 |
| 2009/0022806 | A1* | 1/2009 | Mousa ................... A61B 6/037 424/489 |
| 2009/0252803 | A1* | 10/2009 | Yuan ..................... A61K 9/5146 424/489 |
| 2011/0052715 | A1* | 3/2011 | Davis et al. .................. 424/499 |
| 2011/0104283 | A1* | 5/2011 | Mousa ................. A61K 9/5146 424/487 |

FOREIGN PATENT DOCUMENTS

| CN | 102716495 | * | 6/2012 |
| CN | 102716495 | * | 10/2012 |

OTHER PUBLICATIONS

Ason et al. "Improved efficacy for ezetimibe and rosuvastatin by attenuating the induction of PCSK9".Journal of Lipid Reseach vol. 2, 2011 pp. 679-687.*
Chan et al. "Synthesis and Characterization of chitosan-g-poly(ethylene glycol)-folate as non-viral carrier for tumor-targeted gene delivery" (2006).*
Ghiamkazemi et al. "Synthesis, and Characterization, and Evaluation of Cellular Effects of the FOL-PEG-gPEI-GAL Nanoparticles as Potential Non-Viral Vector for Gene Delivery" (2010).*
Ason et al. "Improved efficacy for ezetimibe and rosuvastatin by attenuating the induction of PCSK9" (2010).*
Brookes "Compell:Comparative Effects on Lipid Levels of Niaspan and Statins vs other Lipid Therapies" (2006).*
Munarin "New perspectives in cell delivery systems for tissue regeneration: natural-derived injectable hydrogels" 2012.*
Riva et al. "Chitosan and Chitosan Derivates in Drug Delivery and Tissue Engineering". 2011.*
Parveen et al. "Long circulating chitosan/PEG blended PLGA nanoparticle for tumor drug delivery" Nov. 2011.*
Pamujula et al. "Preparation and in-vitro/in-vivo evaluation of surface-modified poly (lactide-co-glycolide) fluorescent nanoparticles" Jan. 2010.*
Reddy et al. "Nanotechnology for therapy and imaging of liver diseases" Dec. 2011.*
Wang et al. Chitosan-Modified PLGA Nanoparticles with Versatile Surface for Improved Drug Delivery Mar. 2013.*
Parveen et al. "Long ciruclating chitosan/PEG blended PLGA nanoparticle for tumor delivery" 2011.*
Pamujula et al. "Preparation and in-vitro/in-vivo evaluation of surface-modified poly(lactide-co-glycolide) fluorescent nanoparticles" Apr. 2010.*
Reddy et al. "Nanotechnology for therapy and imaging if liver diseases" 2011.*
Wang et al. "Chitosan-Modified PLGA Nanoparticles with Versatile Surface for Improved Drug Delivery" Mar. 2013.*
Oster et al. "DNA nano-carriers from biodegradable cationic branches polyesters are formed by a modified solvent displacement method" Apr. 2006.*

(Continued)

*Primary Examiner* — Robert A Wax
*Assistant Examiner* — Danah Al-Awadi
(74) *Attorney, Agent, or Firm* — Schmeiser, Olsen & Watts, LLP

(57) ABSTRACT

A composition and an associated method for hepatic targeted delivery of thyroid receptor beta1 (TRβ1) agonist to a liver of a subject. The composition includes hydrophobic nanoparticles, a liver targeting moiety exterior to each nanoparticle and covalently bonded to each nanoparticle, and at least one TRβ1 agonist encapsulated within each nanoparticle. The nanoparticles include chitosan hybrid nanoparticles, amine-modified PLGA nanoparticles, solid lipid nanoparticles, and combinations thereof. The liver targeting moiety includes Glycyrrhetinic acid (GA), Lactobionic acid (LA), or combinations thereof.

20 Claims, 17 Drawing Sheets

(56) References Cited

OTHER PUBLICATIONS

Ason et al. "Improved efficacy for ezetimibe and rosuvastatin by attentuating the induction of PCSK9" Jan. 2011.*
Brookes "Compell:Compartive Effects on Lipid Levels of Niaspan and Statins vs other Lipid Therpapies" Jul. 2006.*
Riva et al. "Chitosan and Chitosan Derivatives in Drug Delivery and Tissue Engineering" Aug. 2011.*
Munarin et al. "New perspectives in cell delivery systems for tissue regeneration:natural-derived injectable hydrogels" Jul. 2012.*
Chan et al. "Synthsis and characterization of chitosan-g-poly(ethylene glycol)-folate as non-viral carrier for tumor-targeted gene delivery" Jul. 2006.*
Ghiamkazemi et al. "Synthesis, and Characterization, and Evaulauation of Cellular Effects of the FOL-PEG-g-PEI-GAL Nanoparticles as a Potential Non-Viral Vector for Gene Delivery" 2010.*

* cited by examiner (A) Selected examples of TR beta1 agonists (GC-1 and KB-2115) for Nano-hepatic targeting and (B) Hepatic Targeting molecules used, including GA and LA.

Representative confocal images illustrating the uptake of FITC-labeled SLN (solid lipid nanoparticles Conjugated with GA) by cell lines for (A) HepG2 and (B) Endothelial Cells.

(A) Schematic showing the synthetic steps for the Chitosan hybrid Nanoparticles and (B) Illustration of the conjugation of GA and/or LA to the NH2 amine group of chitosan.

Size measurement by DLS: PLGA-PEG NPs encapsulating KB2115

Size measurement by DLS: PLGA-PEG NPs encapsulating KB2115 conjugated with GA/LA.

HPLC chromatograms of KB2115 in standard solution and in nano-formulations

Pharmacokinetics (A) and (B) uptake of KB2115 or nano-KB2115 formulations into liver.

High-fat diet (HFD)-induced dyslipidemia mouse model.

Effect on Total Cholesterol in High Fat Diet Mice after Three Weeks of Daily Treatment

NANOFORMULATION AND METHODS OF USE OF THYROID RECEPTOR BETA1 AGONISTS FOR LIVER TARGETING

CROSS-REFERENCES TO RELATED APPLICATIONS

This patent application claims priority to U.S. Provisional No. 61/669,725, filed on Jul. 10, 2012, which is incorporated herein by reference in its entirety.

TECHNICAL FIELD

This invention pertains to methods and compositions of Nano-hepatic targeting mechanisms for lipid and triglyceride lowering and body weight loss in dyslipidemia, familial hypercholesterolemia, diabetes, and obese subjects with high cardiovascular risk.

BACKGROUND

According to the American Heart Association, atherosclerosis, partly because of high cholesterol (hypercholesterolemia) and triglyceride (hypertriglyceridemia), is the leading cause of cardiovascular diseases. Although statins (HMG CoA reductase inhibitors) significantly reduce cardiovascular-related morbidity and mortality in patients with and without coronary artery disease, they have been shown to cause liver damage in some people, particularly those needing high doses or combination therapy. Only 38% of these patients achieved the low-density lipoprotein cholesterol goals set by the National Cholesterol Education Program and more aggressive treatment of dyslipidemia is needed. Among the patients in need of alternatives to statin therapies are those who cannot tolerate statins, are resistant to statins and those with familial hypercholesterolemia. In familial hypercholesterolemia patients, where 1 in every 500 children is born with abnormal lipid profiles that predispose them to premature arteriosclerosis, a potent lipid lowering or combinations of agents might be required.

Thyroid hormones affect most mammalian tissues. In excess, these hormones may cause weight loss, tachycardia, atrial arrhythmias, and heart failure. Further physiological responses are reduction of plasma cholesterol levels, elevated mood, and muscle wasting (Utiger R D (1995): The thyroid: physiology, thyrotoxicosis, hypothyroidism, and the painful thyroid, In: Felig P F, Baxter J D, Frohman C A (eds) Endocrinology and Metabolism, MacGraw-Hill, New York, pp 435-519). Some effects of thyroid hormones could be beneficial; e.g. lowering plasma cholesterol levels or inducing weight loss in obese individuals. Other effects, such as promotion of tachycardia and subsequent heart failure, are deleterious and can outweigh beneficial properties of thyroid hormone analogs (von Olshausen K, Bischoff S, Kahaly G, Mohr-Kahaly S, Erbel R, Beyer J, Meyer J (1989): Cardiac arrhythmias and heart rate in hyperthyroidism, Am J Cardiol 63:930-933). If hormone analogs could be made to be selective in their effects, adverse actions of thyroid hormone might be avoided. The thyroid receptor beta1 (TR$\beta_1$) and thyroid receptor beta2 (TR$\beta_2$) isoforms differ in their amino termini, but both bind and respond to thyroid hormone. Selective modulation of thyroid receptor (TR) action might be useful in treating obesity and hypercholesterolemia and other lipid disorders. GC-1 and KB-2115 has been shown to lower serum cholesterol and triglyceride, risk factors for atherosclerosis (Trost S U, Swanson E, Gloss B, Wang-Iverson D B, Zhang H, Volodarsky T, Grover G J, Baxter J D, Chiellini G, Scanlan T S, Dillmann W H (2000): The thyroid hormone receptor-β-selective agonist GC-1 differentially affects plasma lipids and cardiac activity, Endocrinology 141:3057-3064; Berkenstam A, Kristensen J, Mellstrom K, Carlsson B, Malm J, Rehnmark S, Garg N, Andersson C, Rudling M, Sjoberg F, Angelin B, Baxter J (2008): The thyroid hormone mimetic compound KB2115 lowers plasma LDL cholesterol and stimulates bile acid synthesis without cardiac effects in humans, Proc. Natl. Acad. Sci. USA 105, 663-667; Scanlan T (2010): Sobetirome: a case history of bench-to-clinic drug discovery and development, Heart Fail. Rev. 15, 177-182).

Pharmacological approaches to selectively stimulate TR$\beta$1 activity are based on the development of compounds that interact with the C-terminal LBD and modulates receptor activity. KB2115 (eprotirome) is another TR$\beta$1 selective compound that has been tested in humans (Berkenstam A, Kristensen J, Mellstrom K, Carlsson B, Malm J, Rehnmark S, Garg N, Andersson C, Rudling M, Sjoberg F, Angelin B, Baxter J (2008): The thyroid hormone mimetic compound KB2115 lowers plasma LDL cholesterol and stimulates bile acid synthesis without cardiac effects in humans, Proc. Natl. Acad. Sci. USA 105, 663-667). Eprotirome was administrated to moderately overweight and hypercholesterolemic subjects for two weeks. Serum total and LDL cholesterol as well as apoB levels were reduced without detectable effects on the heart (Taylor A, Stephan Z, Steele R, Wong N (1997): Beneficial effects of a novel thyromimetic on lipoprotein metabolism, Mol. Pharmacol. 52, 542-547). Bile acid synthesis serves as the major elimination route of excess cholesterol indicating that eprotirome induced net cholesterol efflux. Eprotirome has also been tested in combination with either ezetimibe or statin therapy in hyper-cholesterolemic patients. GC-1 was shown to be effective in lowering serum cholesterol and triglyceride in Phase I clinical trial. However, a recent animal toxicology study demonstrated unwanted effects following mid to long-term exposure halting the advancement of the whole TR beta1 agonist class. Cartilage damage was observed in dogs given eprotirome for up to 12 months. This cartilage damage occurred in all animals treated with high doses but was also seen in the lower dose groups, while control animals displayed no damage. Unfortunately, this undesirable side effect has jeopardized the use of thyromimetic as a general therapy for hypercholesterolemia and other lipid disorders.

BRIEF SUMMARY

The present invention provides a composition for hepatic targeted delivery of thyroid receptor beta1 (TR$\beta$1) agonist to a liver of a subject, said composition comprising:

hydrophobic nanoparticles, wherein the nanoparticles are selected from the group consisting of chitosan hybrid nanoparticles, amine-modified poly (lactic-co-glycolic acid) (PLGA) nanoparticles, solid lipid nanoparticles, and combinations thereof;

a liver targeting moiety exterior to each nanoparticle and covalently bonded to each nanoparticle, said liver targeting moiety selected from the group consisting of Glycyrrhetinic acid (GA), Lactobionic acid (LA), and combinations thereof; and at least one TR$\beta$1 agonist encapsulated within each nanoparticle.

The present invention provides a method for targeted delivery of thyroid receptor beta1 (TR$\beta$1) agonist to a liver of a subject, said method comprising administering a composition to the subject, said composition comprising:

hydrophobic nanoparticles, wherein the nanoparticles are selected from the group consisting of chitosan hybrid nanoparticles, amine-modified poly (lactic-co-glycolic acid) (PLGA) nanoparticles, solid lipid nanoparticles, and combinations thereof;

a liver targeting moiety exterior to each nanoparticle and covalently bonded to each nanoparticle, said liver targeting moiety selected from the group consisting of Glycyrrhetinic acid (GA), Lactobionic acid (LA), and combinations thereof; and at least one TRβ1 agonist encapsulated within each nanoparticle with or without known anti-dyslipidemia agents from the statin class, inhibitors of PCSK9, Niacin, fibrate, and combination thereof.

DETAILED DESCRIPTION

The present invention provides a safe and effective LDL-lowering agent (s) via novel nano-hepatic targeting approaches. To solve the toxicity problem, the present invention uses a nanotechnology platform to target KB-2115, GC-1 analog and other thyroid receptor beta1 (TRβ1) selective agonists, with or without statin, anti-PCSK9 and other LDL-C lowering mechanisms, for differential targeted delivery to the liver in order to minimize its systemic distribution.

Figure 1:
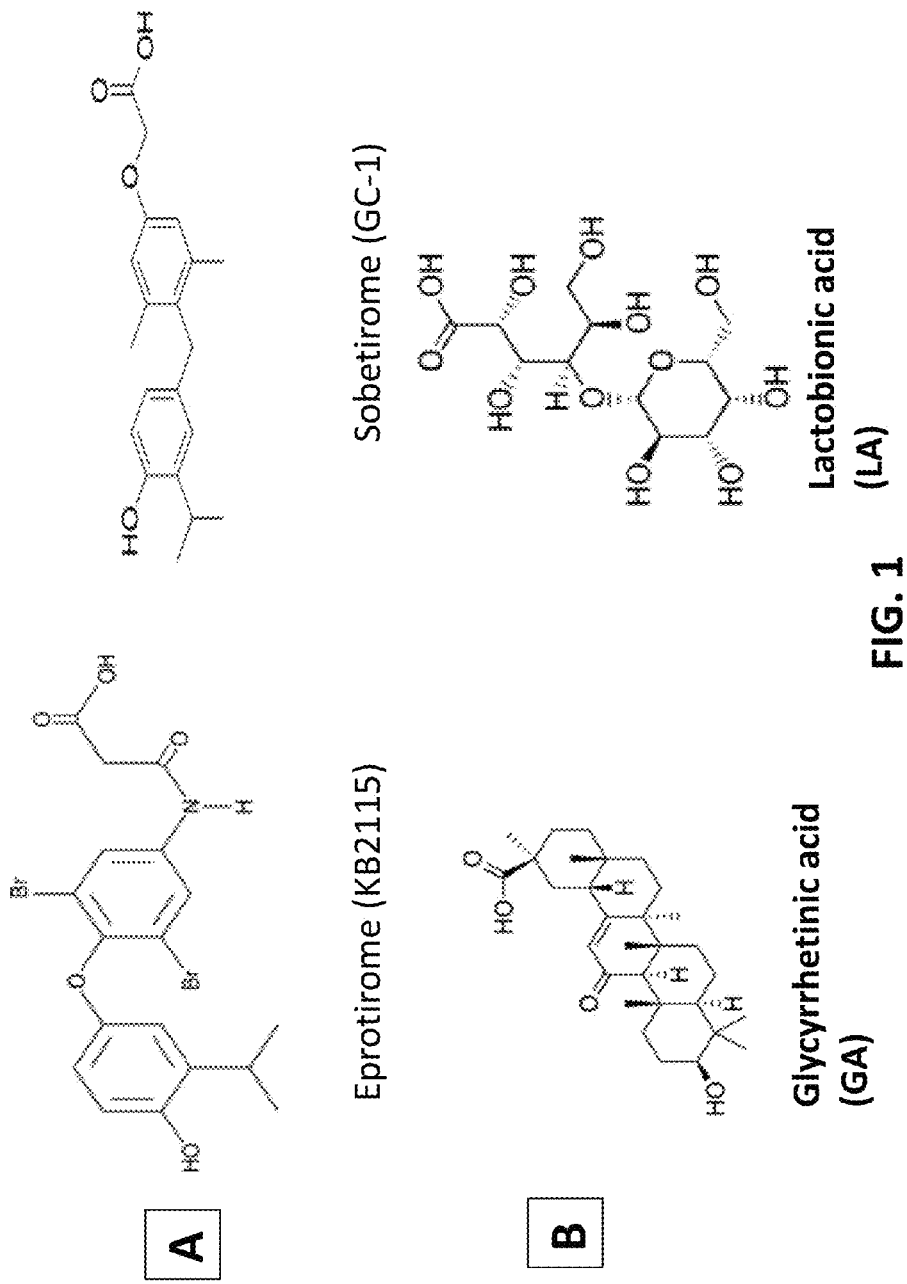
FIG. 1 depicts selected examples of (A) thyroid receptor beta1 agonists and (B) hepatic targeting moieties, in accordance with embodiments of the present invention.

FIG. 1 depicts selected examples of: (A) thyroid receptor beta1 agonists (KB2115 and GC-1) and (B) hepatic targeting moieties (Glycyrrhetinic acid (GA) and Lactobionic acid (LA)), in accordance with embodiments of the present invention.

Nanoformulations of thyroid receptor beta1 agonist or stimulator for hepatic targeting in lowering LDL-cholesterol would provide improved efficacy and safety with regards to systemic adverse effects. Unlike the statin class of drugs which decrease cholesterol synthesis, thyroid receptor beta1 agonists such as GC-1, KB2115 or others stimulates cholesterol catabolism to bile acids without affecting cholesterol synthesis. Nano hepatic targeted TRβ1 agonists could be combined with the Peroxisome Proliferator-Activated Receptor Agonists (PPAR) such as fibrate and/or Nicotinic acid. Additionally, Nano hepatic targeted TRβ1 agonists could be combined with statins or PCSK9 inhibitor. Nano-encapsulation into hydrophobic nanoparticles including amine-modified poly (lactic-co-glycolic acid) (PLGA), Docosahexaenoic acid (DHA), eicosapentaenoic acid (EPA), EPA/DHA, solid lipid nanoparticles using HDL with or without cross linkage to chitosan. Low to ultralow molecular weight chitosan is conjugated to fatty acids (including, but not limited to, EPA, DHA, or combinations in different amounts), other acids (amino acids, hyaluronic acid, and linoleic acids) leading to the generation of hydrophobic polymer that still retain mucoadhesive properties and positive charges for long residence time on cell membranes. Encapsulation of TRβ1 agonists into hydrophobic PLGA with or without chitosan and polyethylene glycol (PEG), chitosan-EPA, chitosan-DHA or chitosan EPA/DHA nanoparticles as well solid lipid nanoparticles conjugated to hepatic targeting moieties such as Glycyrrhetinic acid and/or Lactobionic acid were carried out.

Example 1: Cell Based Transactivation Assay for TRβ

A standard TRβ cell based assay was used. The TRβ Reporter Assay System provides constitutive, high-level expression of Human Thyroid Hormone Receptorβ, a ligand-dependent transcription factor. Because these cells incorporate a responsive luciferase reporter gene, quantifying expressed luciferase activity provides a sensitive surrogate measure of TRβ1 activity in the treated cells.

Example 2: Test for LDLR Up-Regulation

Use of a recombinant assay that demonstrates that expression of LDLR) constructs in HEK-293 cells resulted in the high expression level of intracellular LDLRs. The expression vector of human LDLR was constructed under the control of the cytomegalovirus promoter-enhancer (pCMV-LDLR). These constructs were used to transiently transfect mammalian cells, and cells were subjected to SDS-PAGE and immunoblot analysis using an LDLR antibody. The data shows that cells that were transfected with only pCMV-LDLR show expression of the LDLR in the cells. Using this assay, compounds were tested for their ability to reduce the degradation of the LDLR. HEK-293 cells grown in 96-well plates overnight and transfected with LDLR were used. Compounds dissolved in DMSO or vehicle were added to the culture media, and incubated for 24-48 hours. The cells were then lysed. Both cell lysate and supernatant are subjected to quantitation using the above immunoassay. Compounds that increase the up-regulation of LDLR were selected. A similar assay was implemented using the HepG2 cells, since these cells express the LDLR endogenously.

None of the TR beta agonists including GC-1, KB-2115 or their nanoformulations resulted in any significant changes in LDLR up-regulation in either HEK-239 cells or HepG2 cells. These data suggest that TR beta agonist work by different mechanism other than LDLR. The major mechanism appears to be the stimulation of cholesterol catabolism to bile acids without affecting either cholesterol recycling (operated by PCSK9 inhibitors) via the LDLR or the cholesterol synthesis (operated by statins via the inhibition of HMG-CoA reductase).

Example 3: Test for Cell Viability and Hepatic Uptake

HEK-293T cells or HepG2 cells were seeded in 96-well plates in a cell media containing 10% Fetal Bovine Serum and incubated overnight at 37° C. Compounds at various concentrations were added to cells after 24 hours and incubated for an additional 48 hours. Cell viability was assayed using Resazurin (Sigma 199303) and an Envision 2101 Multi-label plate reader.

Hepatic uptake in real time was be tested by confocal imaging and determination of levels of TRβ1 agonist in the HepG2 cells by LC/MS/MS method.

Figure 2:
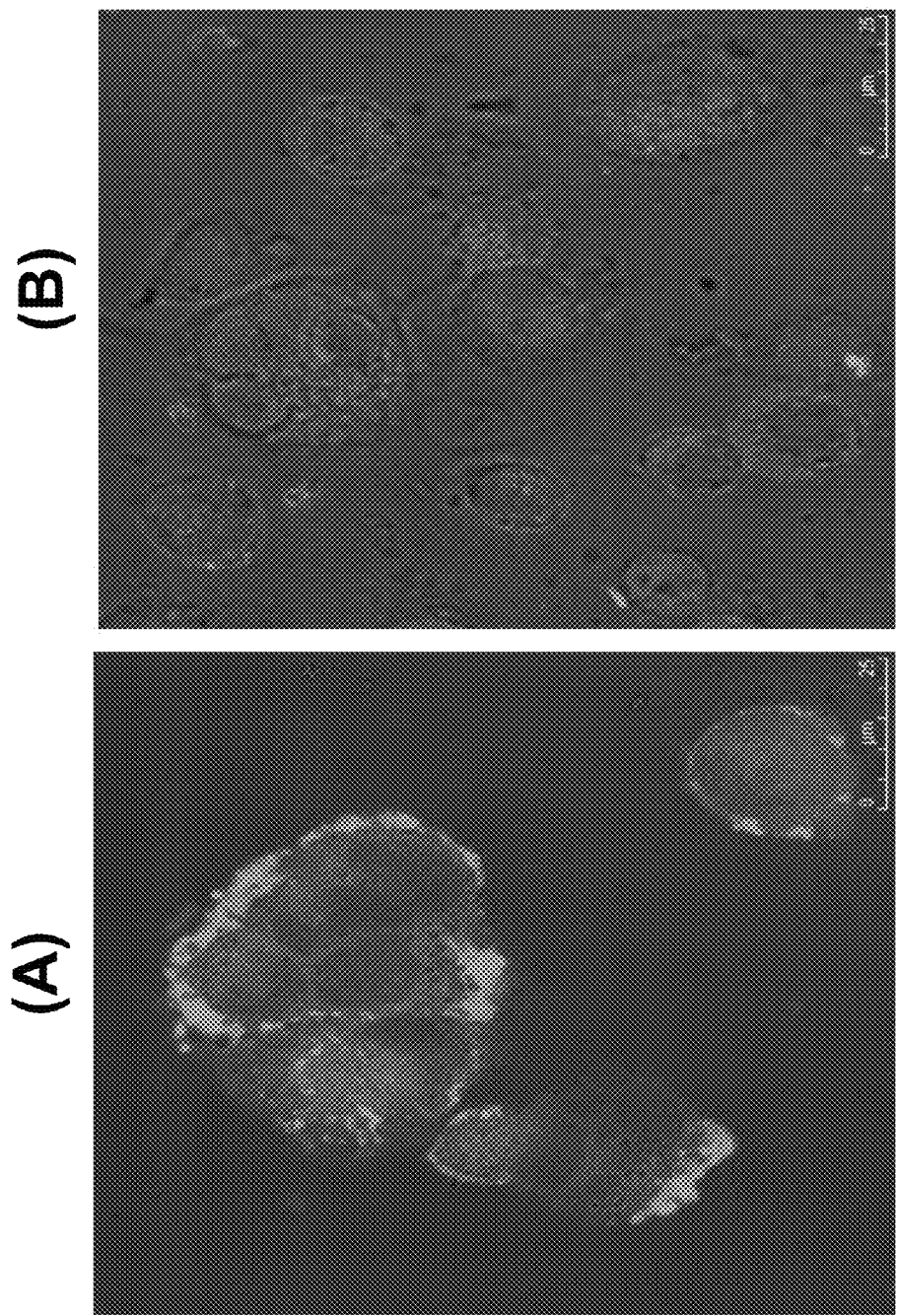
FIG. 2 depicts representative confocal images illustrating the differential uptake of FITC-labeled solid lipid nanoparticles conjugated with Glycyrrhetinic acid (GA) by cell lines for (A) HepG2 but not (B) by other cells such as endothelial cells, in accordance with embodiments of the present invention.

FIG. 2 depicts representative confocal images illustrating the uptake of FITC-labeled solid lipid nanoparticles conjugated with Glycyrrhetinic acid (GA) by cell lines for (A) HepG2 and (B) endothelial cells. FIG. 2 illustrates differential hepatic uptake in HepG2 cells versus other cells for Nano-hepatic targeting of TR beta1 agonist encapsulated into Solid Lipid Nanoparticles (SLN) and conjugated with Glycyrrhetinic acid (GA), Lactobionic acid (LA) or both GA and LA.

The present invention provides nanoformulations for hepatic targeted delivery, processes for synthesis of copolymers encapsulating TRβ1 agonist and conjugating hepatic targeting moiety, processes for synthesis of copolymers of PLGA-Chitosan or solid lipid nanoparticle containing the TRβ1 agonist with or without other lipid modulators such as atorvastatin or anti-PCSK9, niacin or fibrate, and conjugated to hepatic targeting molecules such as Glycyrrhetinic acid, Lactobionic acid or both.

Example 4: Chitosan Hybrid Nanoparticles Targeted with GA and/or LA Encapsulating TRβ1 Agonists For synthesis and optimization of GC-1 and Eprotirome KB-2115 nanoformulation for hepatic targeting, nanoparticle (NP) formulations of GC-1 and Eprotirome KB-2115 were encapsulated into chitosan-linked to fatty acids NPs and into chitosan NPs conjugated with Glycyrrhetinic acid (GA) and/or Lactobionic acid (LA) for optimal pharmacokinetic biodistribution. The synthetic steps included mixing vegetarian mushroom derived GMP Chitosan (KitoZyme S. A., Belgium). Mushroom derived ultra-pure chitosan having different molecular weight ranges (30,000-60,000, 60,000-120,000, and 140,000-220,000 Dalton) were used in the synthesis of the hybrid nanoparticles conjugated to different fatty acids including linolenic acid, deoxycholic acid, aliginic acid, Poly(lactic-co-glycolic acid) (PLGA), omega-3 fatty acids of eicosapentaenoic acid (EPA) and/or Docosahexaenoic acid (DHA), and hyaluronic acid (HA). The ratio of chitosan to the different acid listed above ranged from 1/1 to 10/1, and preferably 5/1 for optimal hydrophobicity, of the nanoparticle in order to attain greater than 70% loading of the hydrophobic TR beta1 agonists, statin, and/or anti-PCSK9. The optimal ratio, for maximal loading of exceeding 70% of TR beta1 agonists and optimal functional NH2 for conjugation with targeting moieties including Lactobionic acid (LA) and/or Glycyrrhetinic acid (GA), ranged from 1/3 to 1/10 w/w (GA and/or LA to Chitosan).

Figure 3:
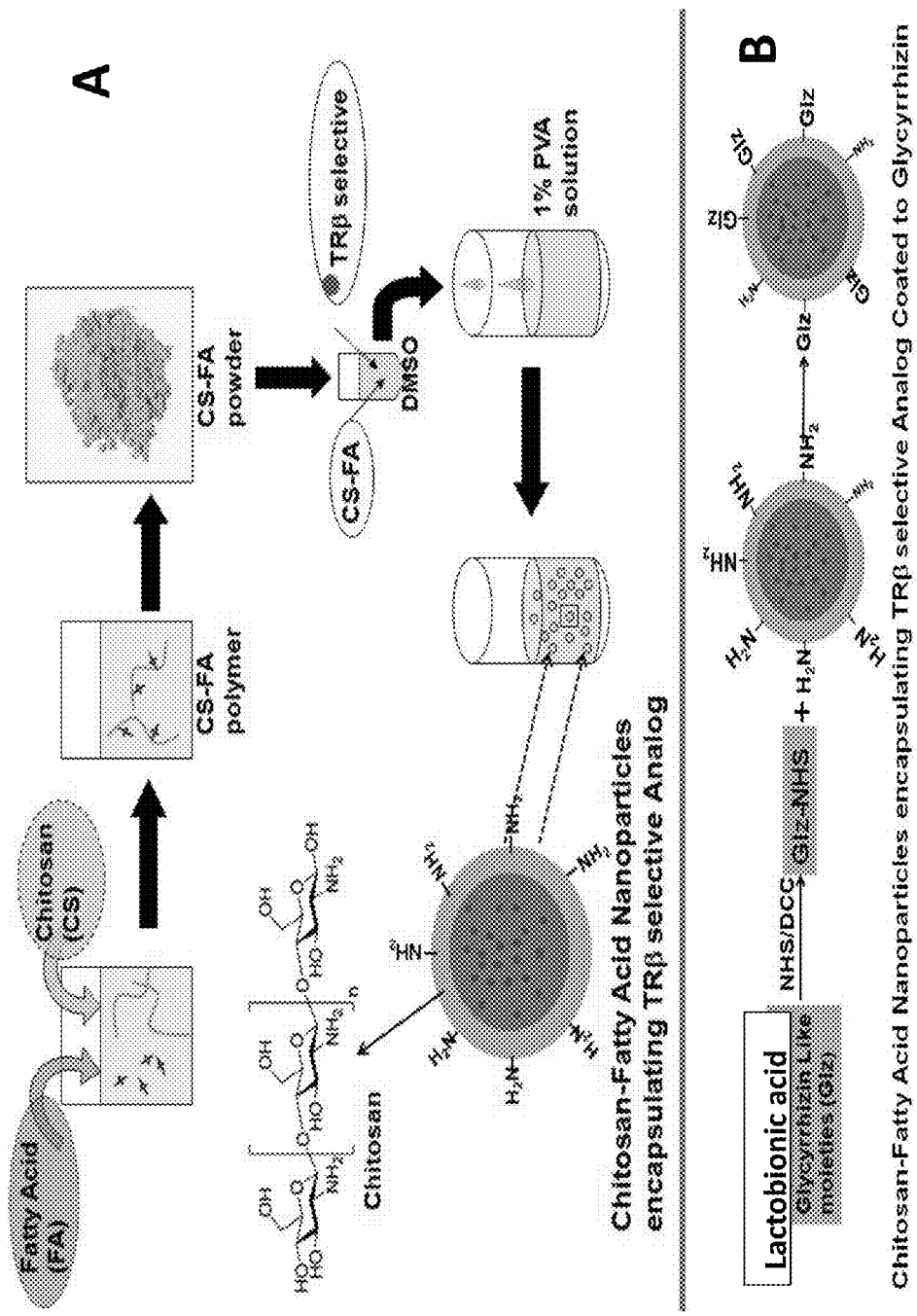
FIG. 3 illustrates (A) a scheme used in the synthesis of fatty acid-Chitosan NP hybrid encapsulating the thyroid receptor beta1 agonist GC-1 and (B) covalent bonding of the hepatic targeting moiety via the reaction between the Chitosan —NH2 and the Lactobionic acid (LA) and/or Glycyrrhetinic acid (GA) for hepatic targeting, in accordance with embodiments of the present invention.

FIG. 3 illustrates (A) a scheme used in the synthesis of fatty acid-Chitosan NP hybrid encapsulating the thyroid receptor beta1 agonist GC-1 and (B) covalent bonding of the hepatic targeting moiety via the reaction between the Chitosan —NH2 and the Lactobionic acid and/or Glycyrrhetinic acid for hepatic targeting, in accordance with embodiments of the present invention, which followed by the release of the TR beta1 agonist GC-1, KB-2115 or their analogs. Panel (A) of FIG. 3 shows the synthetic steps for the chitosan hybrid nanoparticles. Panel (B) of FIG. 3B illustrate the conjugation of GA and/or LA to the NH2 amine group of chitosan hybrid nanoparticles.

Example 5: Measurement of Chitosan Hybrid Nanoparticle Particle Size

Size distributions of chitosan NP encapsulating GC-1 or KB-2115 were determined by using a Malvern Zetasizer (Malvern Instruments, Westborough, Mass.). The nanoparticle dispersion (1 mL) was placed in a 4-sided clear plastic cuvette and analyzed at 25° C.

Figure 4:
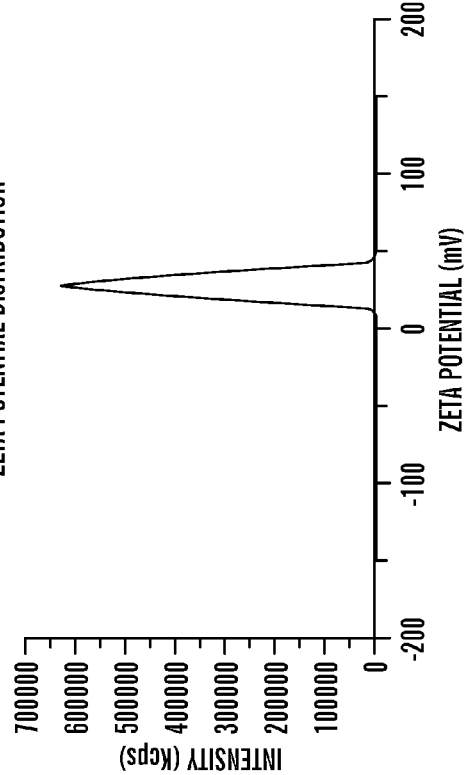
FIG. 4 shows the size and zeta potential for GC-1 Chitosan-fatty acid hybrid nanoparticle, in accordance with embodiments of the present invention.
Figure 4:
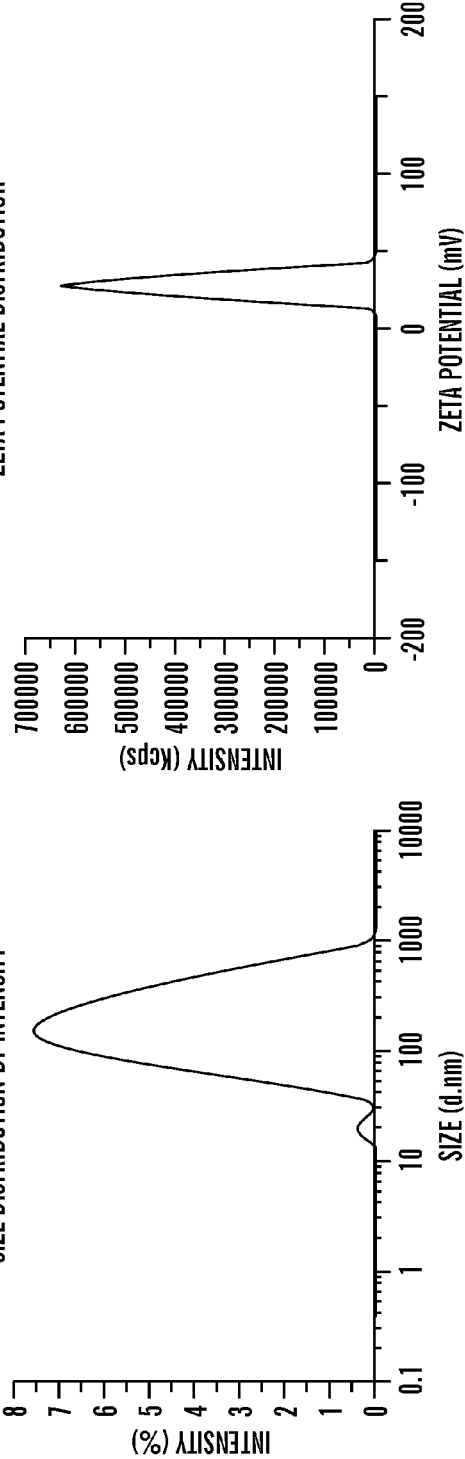

FIG. 4 shows the size and surface charges for GC-1 Chitosan-fatty acid hybrid nanoparticle, in accordance with embodiments of the present invention. The average size is 138 nm and the zeta potential is +27 my, with a loading capacity of about 70% of total GC-1 added as determined by HPLC-UV method.

Example 6: Synthesis of PLGA-NH2 Nanoparticles Targeted with GA and/or LA Encapsulating TRβ1 Agonists A carboxyl terminal end of poly (D,L-lactic-co-glycolic acid) (PLGA) was functionalized with a primary amine group by conjugating hexaethylene glycol-diamine. This scheme, which is similar to the scheme described in FIG. 3, was applied for the synthesis of PLGA NP encapsulating GC-1 or KB-2115 and coated with GA and/or LA for hepatic targeting. The PLGA-NH2 polymeric carrier containing TR beta1 agonist was prepared employing an emulsification-diffusion method. The preparation method included emulsifying a solution of polymer and drug in the aqueous phase containing stabilizer of Polyethylene glycol (PEG).

Figure 5A:
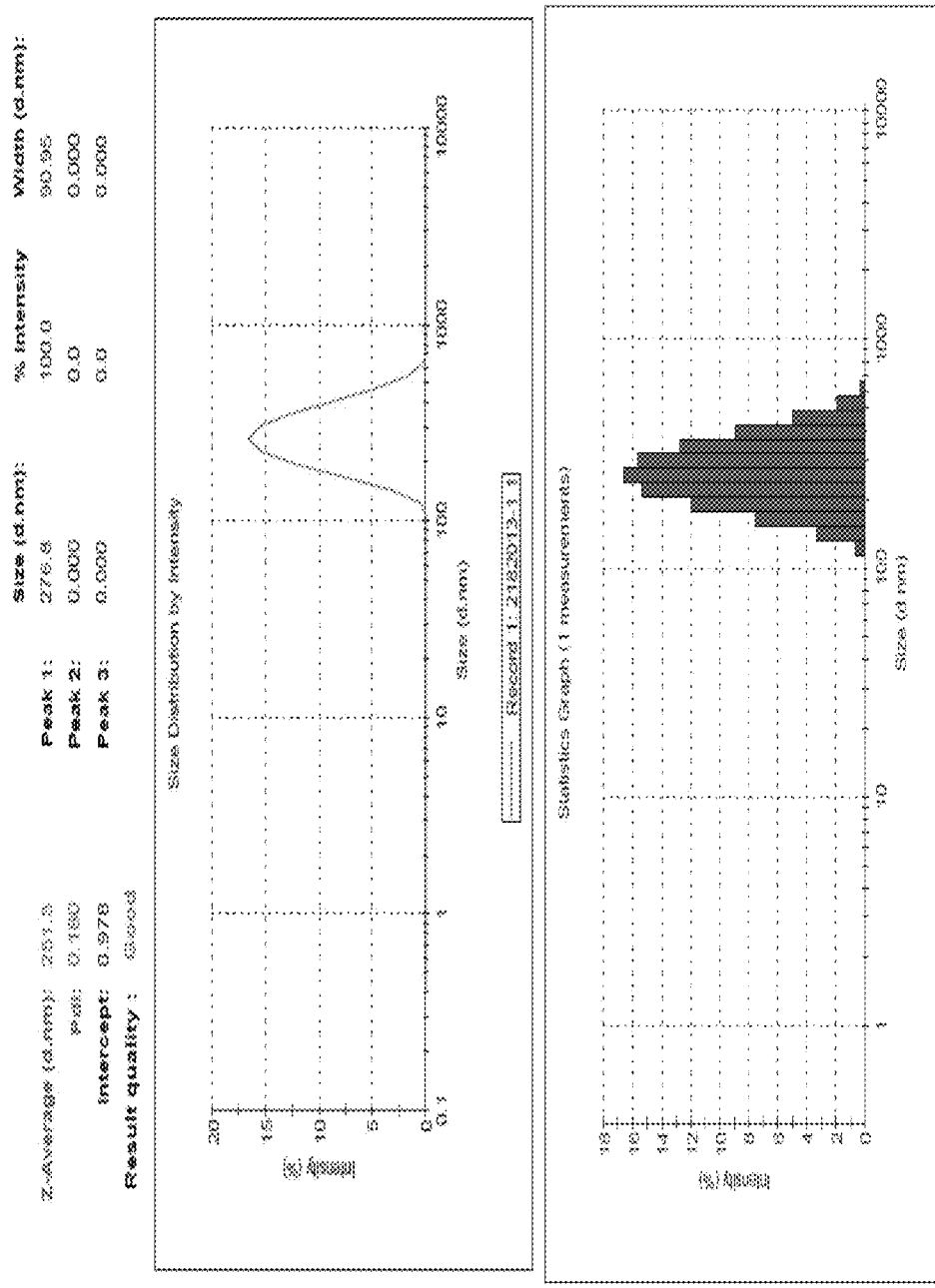
FIG. 5A illustrates the size measurements of PLGA-PEG nanoparticles without GA and/or LA conjugation and encapsulating the TRβ1 agonist KB-2115, in accordance with embodiments of the present invention.

FIG. 5A illustrates the Size Measurements of PLGA-PEG nanoparticles with or without GA and/or LA conjugation and encapsulating KB-2115, in accordance with embodiments of the present invention. In FIG. 5A, the average nanoparticle size is 251 nm.

Figure 5B:
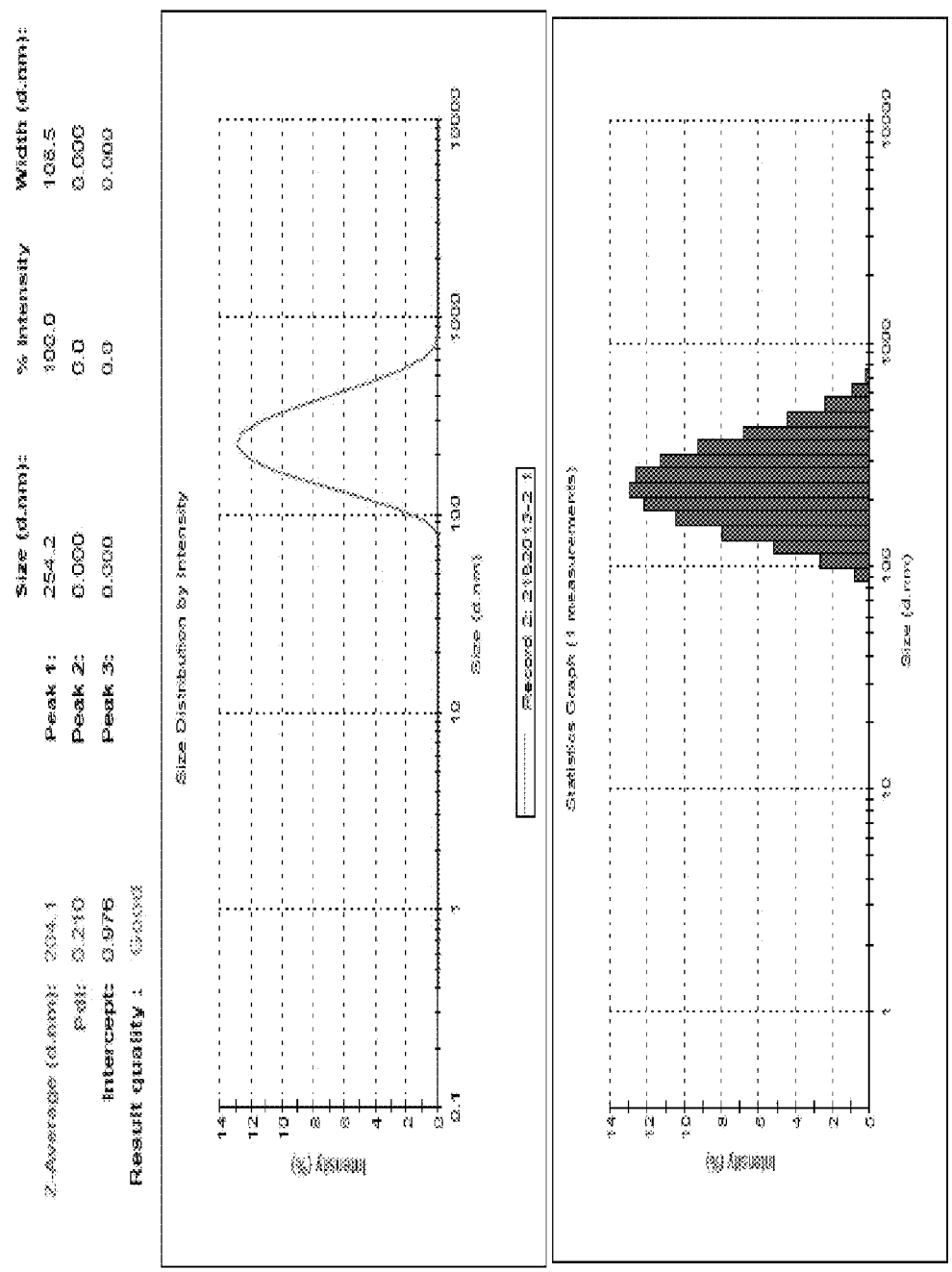
FIG. 5B illustrates the size measurements of PLGA-PEG nanoparticles encapsulating the TRβ1 agonist KB-2115 and conjugated with GA/LA, in accordance with embodiments of the present invention.

FIG. 5B illustrates the Size Measurements of PLGA-PEG nanoparticles encapsulating KB-2115 and conjugated with GA/LA, in accordance with embodiments of the present invention. In FIG. 5B, the average nanoparticle size is 204 nm.

Example 7: Synthesis of Solid Lipid Nanoparticles Targeted with GA and/or LA Encapsulating TRβ1 Agonists The composition of Solid Lipid Nanoparticles (SLN) was (w/w): 40% cholesterol esters, 18% glycerol trioleate, 8% cholesterol, and 34% 1,2-Distearoyl-sn-Glycero-3-Phosphoethanolamine (DSPE) conjugated Polyethylene Glycol (PEG) (DSPE-PEG). The SLN were prepared using the emulsification/solvent evaporation method. Chloroform solutions of GC-1 or KB-2115 (100 μL, 5 mg/mL), cholesteryl oleate (97 μL, 30 mg/mL), glycerol trioleate (87 μL, 15 mg/mL), cholesterol (60 μL, 10 mg/mL), and DSPE-PEG (250 μL, 10 mg/mL) were mixed. Double-distilled water (5 mL) was added to the mixture followed by homogenization for 1 min to obtain an emulsion. Chloroform was evaporated from the emulsion at 50° C. with stirring for 2 hours. The formulation was sonicated. The dispersion was dialyzed against deionized water for 3 hour. Void SLN with no drug incorporated were also prepared according to this procedure.

Figure 6:
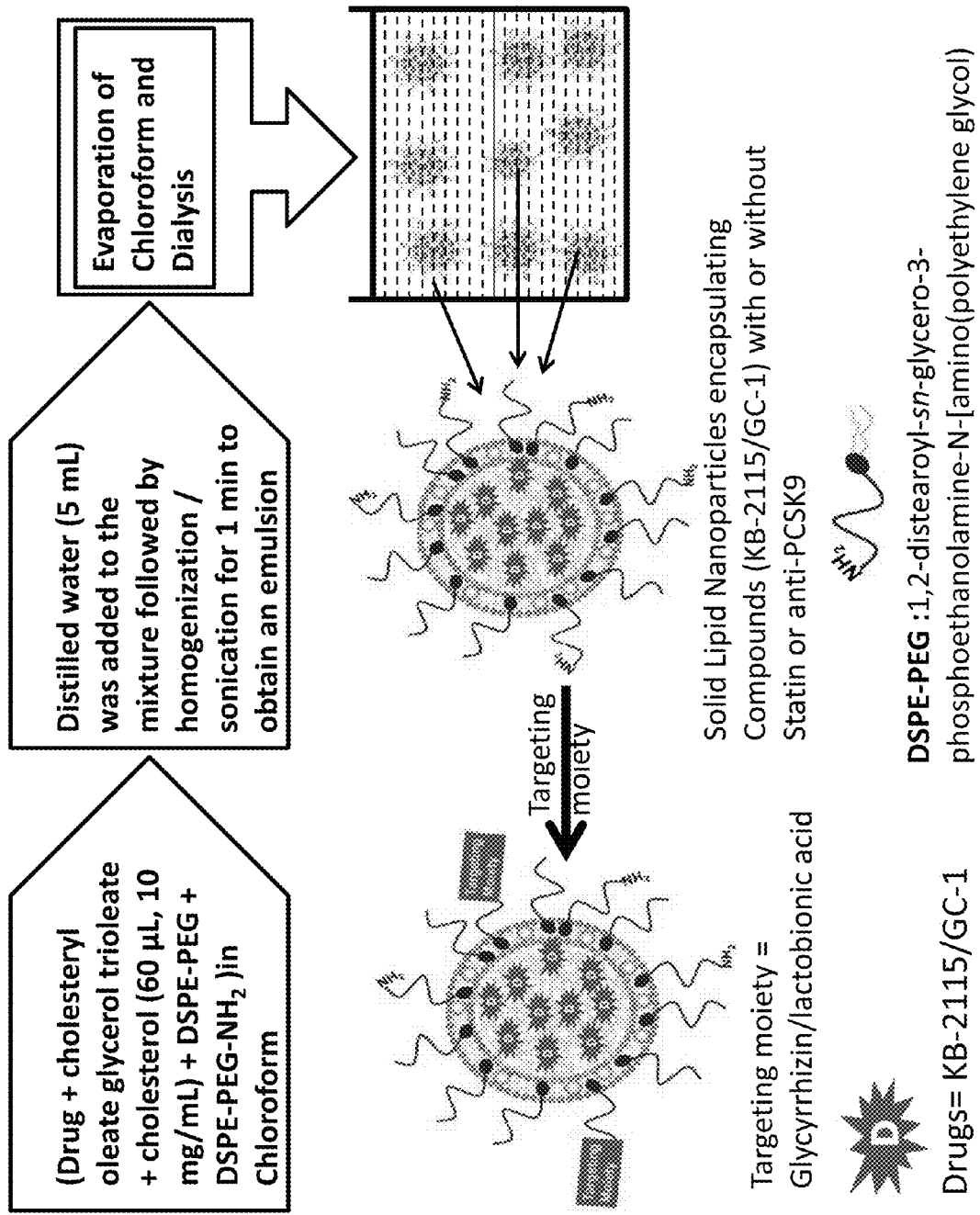
FIG. 6 is a schematic diagram showing the synthesis of solid lipid nanoparticles (SLN), in accordance with embodiments of the present invention.

FIG. 6 is a schematic diagram showing the synthesis of solid lipid nanoparticles (SLN), in accordance with embodiments of the present invention. The SLNs encapsulate with GC-1, KB-2115 with or without atorvastatin or anti-PCSK9 and surface conjugation with GA and/or LA.

Example 8: Measurement of SLN Particle Size

Size distributions of void SLN and SLN encapsulating GC-1 or KB-2115 were determined by using a Malvern Zetasizer (Malvern Instruments, Westborough, Mass.) as described and shown under the synthesis of Chitosan or PLGA NPs.

Example 9: Evaluation of TR Beta1 Agonist (GC-1 or KB-2115) Loading

Transmission electron microscopy (TEM) was used for size confirmation. The nanoformulation were optimized for loading efficiency using high performance liquid chromatography (HPLC)-UV, particle size analysis by dynamic light scattering (DLS) spectroscopy, zeta potential measurement, in vitro release kinetics, accelerated stability at different temperature/humidity, and transmission electron microscopy (TEM) for size confirmation. An aliquot (50 μL) of GC-1 or KB2115-loaded SLN dispersion was dissolved in 950 μL of acetonitrile. Further dilution (1:10) was performed using 70% acetonitrile. The amount of GC-1 or KB-2115 was determined by an LC-MS/MS method. Loading efficiency (%) was calculated using the following formula: Loading efficiency (%)=(amount of GC-1 or KB-2115 in SLN/amount of GC-1 or KB-2115 used in the formulation)×100.

Figure 7:
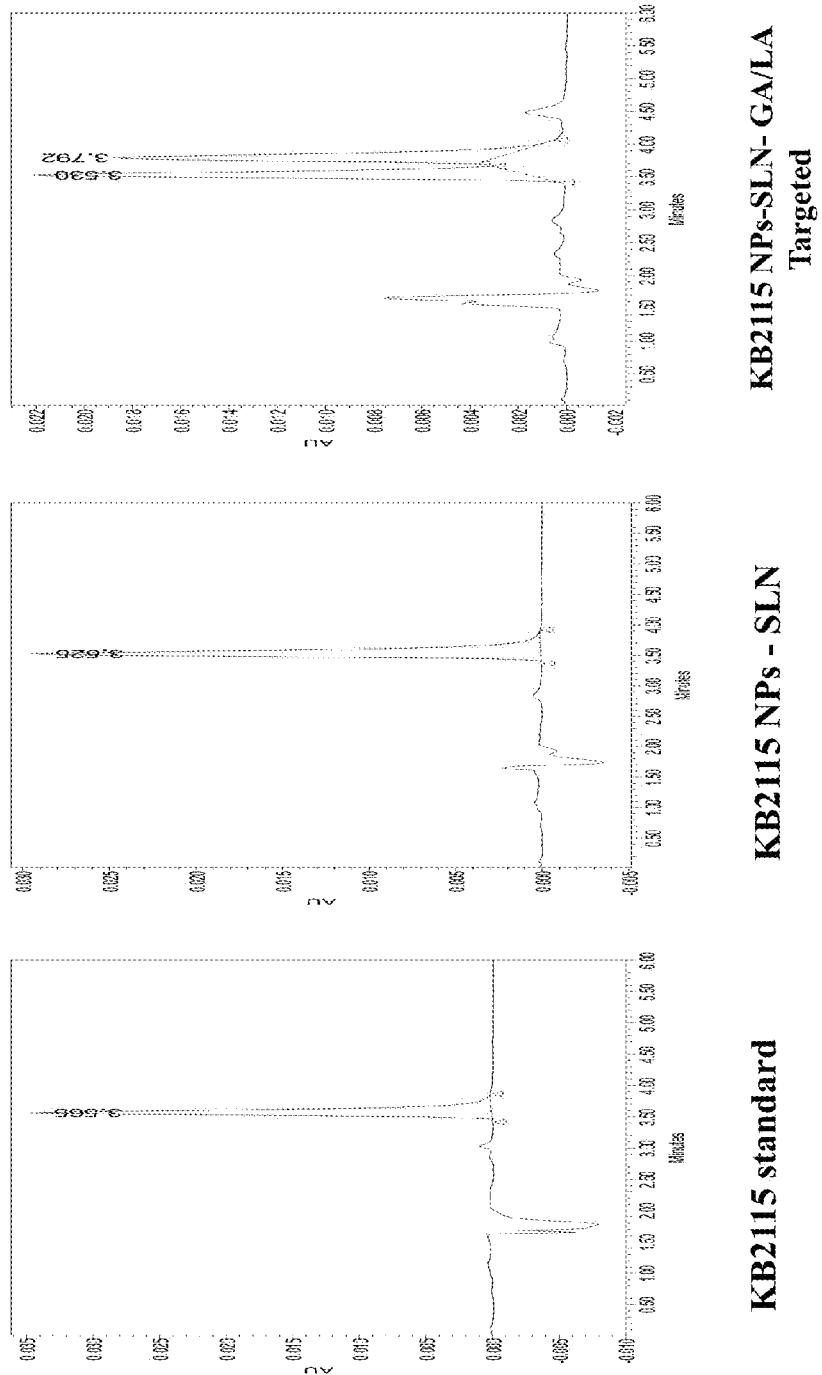
FIG. 7 shows high performance liquid chromatography (HPLC) chromatograms of KB2115 in standard solution and in nano-formulations, in accordance with embodiments of the present invention.

FIG. 7 shows high performance liquid chromatography (HPLC) chromatograms of KB2115 in standard solution and in nano-formulations, in accordance with embodiments of the present invention, assayed on a C18 column with 80% methanol containing 0.2% formic acid as mobile phase, UV: 250 nm. A calibration curve was also established for the analysis of the SLN NPs loading levels in Table 1.

TABLE 1

Loading Level of KB2115 in Nano-Formulations

| Sample code | Mean Peak Area | (Conc.) ug/ml |
|---|---|---|
| NPs-KB2115-SLN Nano | 214323 | 127.80 (85% Loading) |
| NPs-KB2115-SLN Nano-GA/LA | 135432 | 80.51 (74% Loading) |

Example 10: Synthesis of Omega-3-Fatty Acids Such as DHA, EPA or DHA/EPA-Chitosan Nanoparticles Incorporating TRβ1 Agonists Omega-3-fatty acids such as DHA, EPA or DHA/EPA-chitosan nanoparticles incorporating TRβ1 agonists were synthesized by gelation reaction of chitosan with tripolyphophate (TPP) for ionic cross-linking. An amount of DHA, EPA, DHA/EPA-chitosan solutions is combined with an amount of TRβ1 agonists. To this solution, an amount of TPP was added and then after cross-linking, the nanoparticles were isolated by centrifugation. The size of the nanoparticles was determined by dynamic light scattering instrument (DLS) and transmission electron microscopy (TEM). Loading efficiency of a TRβ1 agonist was determined by high performance liquid chromatography (HPLC). Similarly, chitosan/deoxycholate were cross-linked with fatty acids, such as EPA, DHA, EPA/DHA, linolenic acid, or aliginic acid, generating nanoparticles for encapsulation of TRβ1 agonists. The in vitro release kinetics of nanoparticles generated in the above-described process was measured. The release kinetics of DHA/EPA and TRβ1 agonists from chitosan or chitosan/deoxycholate nanoparticles was studied in phosphate buffered saline (PBS, pH 7.4), simulated gastric fluid (SGF, pH 1.2), simulated intestinal fluid (SIF, pH 7.5), human plasma or human serum albumin (HSA). A known amount of DHA/EPA containing TRβ1 agonists conjugated to the nanoparticles was suspended with 20 ml of various media as mentioned above and the solutions was kept at room temperature. At various time intervals, an amount of the suspension containing DHA/EPA-chitosan nanoparticles encapsulating TRβ1 agonists was taken out and centrifuged for 20 minutes at 10,000×g to separate the released DHA/EPA and TRβ1 agonists from the nanoparticles. The centrifugates containing the released DHA/EPA and TRβ1 agonists were analyzed by HPLC.

Example 11: Synthesis of Hybrid Chitosan Polymer Conjugated to Deoxycholic Acid Chitosan polymer was conjugated to deoxycholic acid using carbodimide chemistry via a covalent bond between the —NH2 and —COOH group present in chitosan and deoxycholic acid respectively. Later on, this hybrid chitosan polymer was used to synthesize chitosan-deoxycholic acid nanoparticles (CH-DA-NPs) incorporating TRβ1 agonists. For liver targeting, the nanoformulations below was conjugated with Glycyrrhetinic acid and/or Lactobionic acid. Chitosan-EPA, DHA or EPA/DHA nanoparticles encapsulated TRβ1 agonists as follows.

a) Chitosan-deoxycholate nanoparticles encapsulating TRβ1 agonists;
b) Chitosan-alginate (CS-AL-NPs) nanoparticles encapsulating TRβ1 agonists;
c) Chitosan-arginine (CS-A-NPs)—alginate nanoparticles encapsulating TRβ1 agonists;
d) Chitosan-linolenic acid nanoparticles encapsulating TRβ1 agonists;
e) Chitosan-hyaluronic acid nanoparticles encapsulating TRβ1 agonists;
f) Chitosan-collagen-hydroxyapatite (CL-HA NPs)—alginate nanoparticles encapsulating TRβ1 agonists.

For Chitosan modified nanoparticles coupling with the above acids (a)-(f) was carried out through the 1-ethyl-3-(3-dimethylaminopropyyl) carbodiimide reaction. The loading ability of the hydrophobically modified chitosan (chitosan-fatty acids, amino acids, hyaluronic acid, deoxycholic acid, aliginic acids, and other cross-linkers) is also used for the incorporation of TRβ1 agonists.

In one embodiment, for increased mucoadhesive properties, coating of chitosan or chitosan/deoxycholate is also applied. Coating of the formed nanoparticles with Glycyrrhetinic acid (GA) and/or Lactobionic acid (LA) and other known liver targeting moiety would be utilized. Additionally, chitosan is conjugated to other fatty acids, or acids such as linolenic acid, hyaluronic acid, aliginic acid, or poly (lactic-co-glycolic acid) (PLGA) generating hydrophobic nanoparticles for the encapsulation of TRβ1 agonists.

In another embodiment, hydrophobic polymers, such as omega 3 fatty acids (EPA, DHA, EPA/DHA (1/1), are used to generate hydrophobic nanoparticles encapsulating TRβ1 agonists followed by chitosan or chitosan/deoxycholate coating and then conjugation with Glycyrrhetinic acid and/or Lactobionic acid for liver targeting. Nanoformulations used include hydrophobically modified chitosan (chitosan-fatty acids, hyaluronic acid, aliginic acids, poly (lactic-co-glycolic acid), collagen or combination thereof) incorporating TRβ1 agonists. DHA, EPA or DHA/EPA is covalently linked to chitosan polymer through a cleavable linker, which can be cleaved to release the DHA/EPA and TRβ1 agonists.

Example 12: Labeling of Nanoformulation for Non-Invasive Imaging and Biodistribution Using IVIS Imaging All synthesized nanoformulations were labeled with Cy7 dye-labeled for fluorescent for in vitro and in vivo imaging. NPs were dialyzed through 3500 molecular weight cutoff membrane for 24 hours to remove un-conjugated Cy7 and then lyophilized. The lyophilized powder were re-dispersed and used for further studies. Animals were administered (orally versus Intravenous injection) Cy7-GC-1 or Cy7 KB-2115 NPs targeted with GA and/or LA versus non-targeted. Real time IVIS imaging was carried out to assess biodistribution. Organs and blood samples were removed at the end of the study for quantitative measurements using established LC/MS/MS methods.

Example 13: Pharmacokinetic and Biodistribution

For PK and biodistribution TRβ agonists and their Nano liver-targeted formulations, male C57BL/6 mice, 4-5 weeks old, were housed 5/cage in a room maintained at 20±2° C. with a humidity of 50±10% and a 12 h light-dark cycle. The animals were fed a standard pelleted mouse chow. One IV dose and one oral dose were selected and 20 µl blood samples were collected using anti-coagulated capillary tubes at 5 min, ½, 1, 3, 6 post-administration for PK profiles. Organs including liver, kidney, intestine, and heart were excised for the measurements of TRβ agonist levels using LC/MS/MS.

Figure 8:
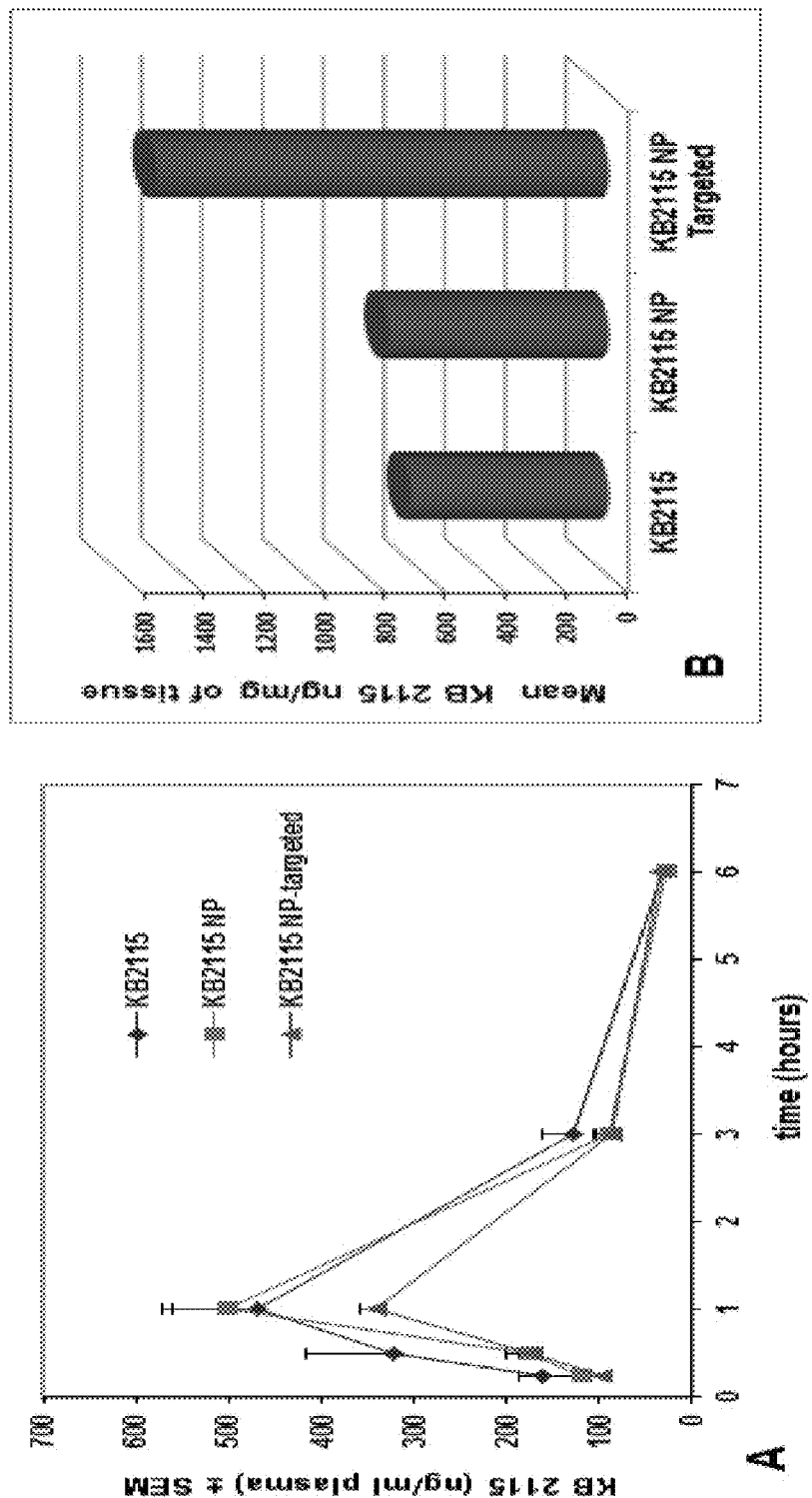
FIG. 8 illustrates the pharmacokinetics (PK) and uptake of KB2115 or nano-KB2115 formulations into liver, in accordance with embodiments of the present invention.

FIG. 8 illustrates the pharmacokinetics (PK) and uptake of KB2115 or nano-KB2115 formulations into liver, in accordance with embodiments of the present invention. Free KB2115, KB2115-SLN NP (un-targeted NP) or KB211 SLN NP5-targeted (Glycyrrhetinic acid acid-coated NP) were administered to mice at 0.35 mg/kg BW, intraperitoneally, n=3 mice per group. Free KB2115, KB2115-NP (un-targeted NP) or KB211 NP5-targeted (Glycyrrhetinic acid acid-coated NP) were administered to mice intraperitoneally at 0.35 mg/kg BW, n=3 mice per group. Blood samples were taken at 0.25, 0.5, 1, 3, and 6 hours after treatment to determine plasma levels of drug alone and in NP formulations. Mice treated with targeted NP show lower KB2115 concentrations in the plasma (orange line) than those treated with untargeted NPs or free KB2115, suggesting the possibility of reduced systemic exposure, while liver-specific delivery is increased. Mice were sacrificed at 6 hours and liver tissue analyzed for KB2115 concentrations by liquid chromatography coupled with tandem mass spectrometry (LC-MS/MS). Surface conjugation of NP with GA and/or LA to increase hepatic-targeting resulted in 3 fold increased drug accumulation in the livers of mice 6 hours after administration (FIG. 8). These data demonstrate the effectiveness of strategies for liver-specific delivery using molecules such as Glycyrrhetinic acid. After these pilot studies were performed, the conjugation process with GA and/or LA and targeting with SLN nanoparticles were improved.

Example 14: Nutritionally-Induced Hypercholesterolemia Model

Mice were fed a high fat diet (TD.06414, Harlan Research Diet, Inc., Indianapolis, Ind.) that provides 60 calories from fat sources increased total cholesterol. The nutritionally induced mouse is therefore a suitable model for examining the effects of Nanoformulated TRβ agonist lead compounds for liver targeting in lowering LDL-C levels. Male C57BL/6 mice were fed either a commercial chow diet (Prolab RMH 3000, PMI feeds, St. Louis, Mo.) to serve as a negative control, or a high fat diet (TD.06414). Plasma was collected once weekly to monitor the level of LDL-C, total cholesterol, HDL-C, and triglyceride. After 4 weeks of feeding the high fat diet, mice were randomly assigned to one of the different groups such that the average LDL-C levels are comparable among the different groups. One group was treated with vehicle, and the other groups are treated with TRβ1 agonist compounds versus its Nano-targeted ones at different doses.

Figure 9A:
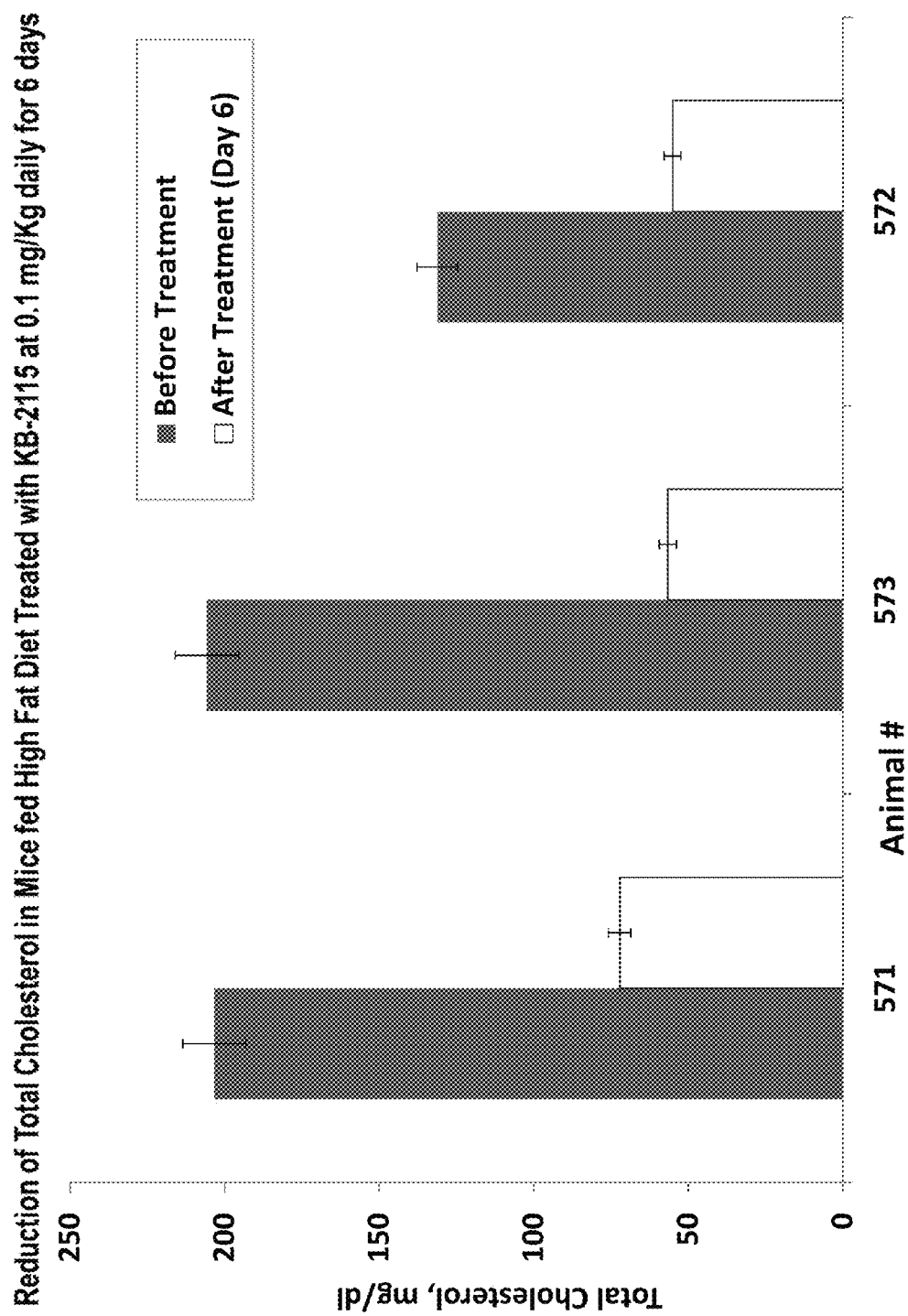
FIGS. 9A and 9B depict the effects of KB-2115 (0.1 mg/kg, Daily for 6 days) on serum total cholesterol in mice fed high fat diet (FIG. 9A) and percent reduction in total cholesterol (FIG. 9B), in accordance with embodiments of the present invention.
Figure 9B:
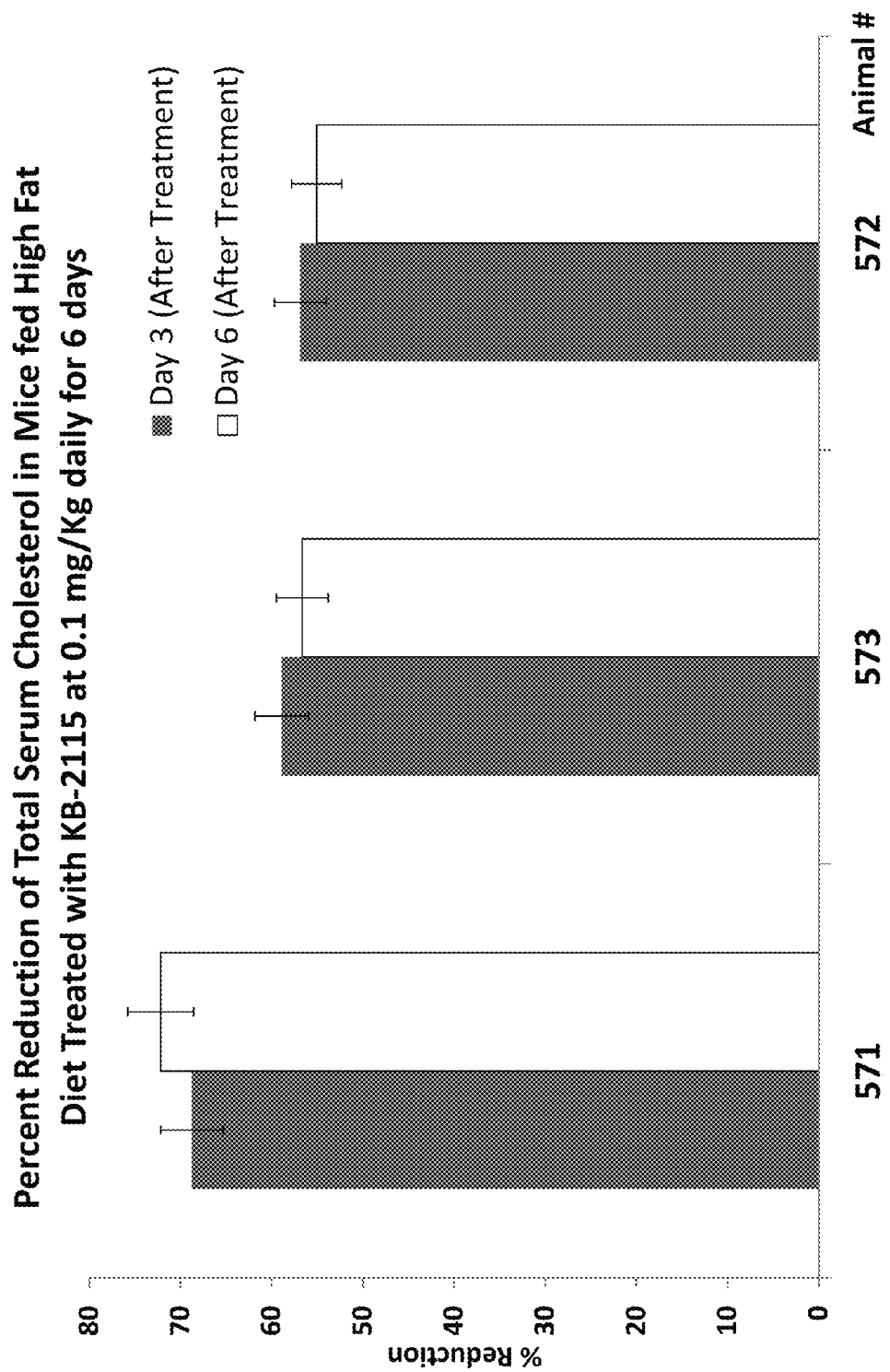

FIGS. 9A and 9B depict the effects of KB-2115 on mice in terms of total cholesterol (FIG. 9A) and percent reduction in total cholesterol (FIG. 9B), in accordance with embodiments of the present invention.

Figure 10A:
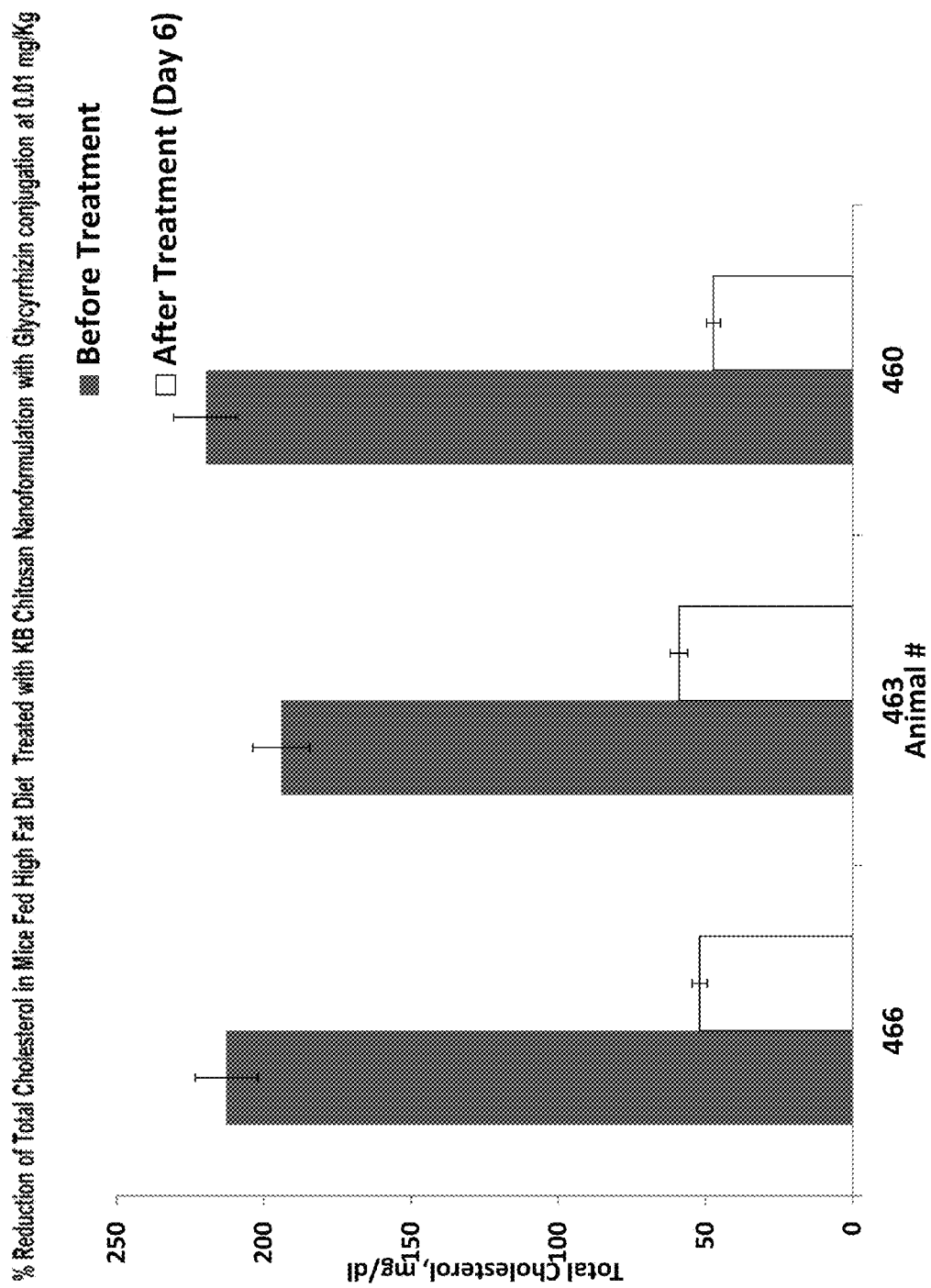
FIGS. 10A and 10B depict the effects of KB-2115, (0.01 mg/kg, daily for 6 days), encapsulated into Chitosan hybrid NP targeted with Glycyrrhetinic acid (GA) on serum total cholesterol in mice fed high fat diet (FIG. 10A) and percent reduction in total cholesterol (FIG. 10B), in accordance with embodiments of the present invention.
Figure 10B:
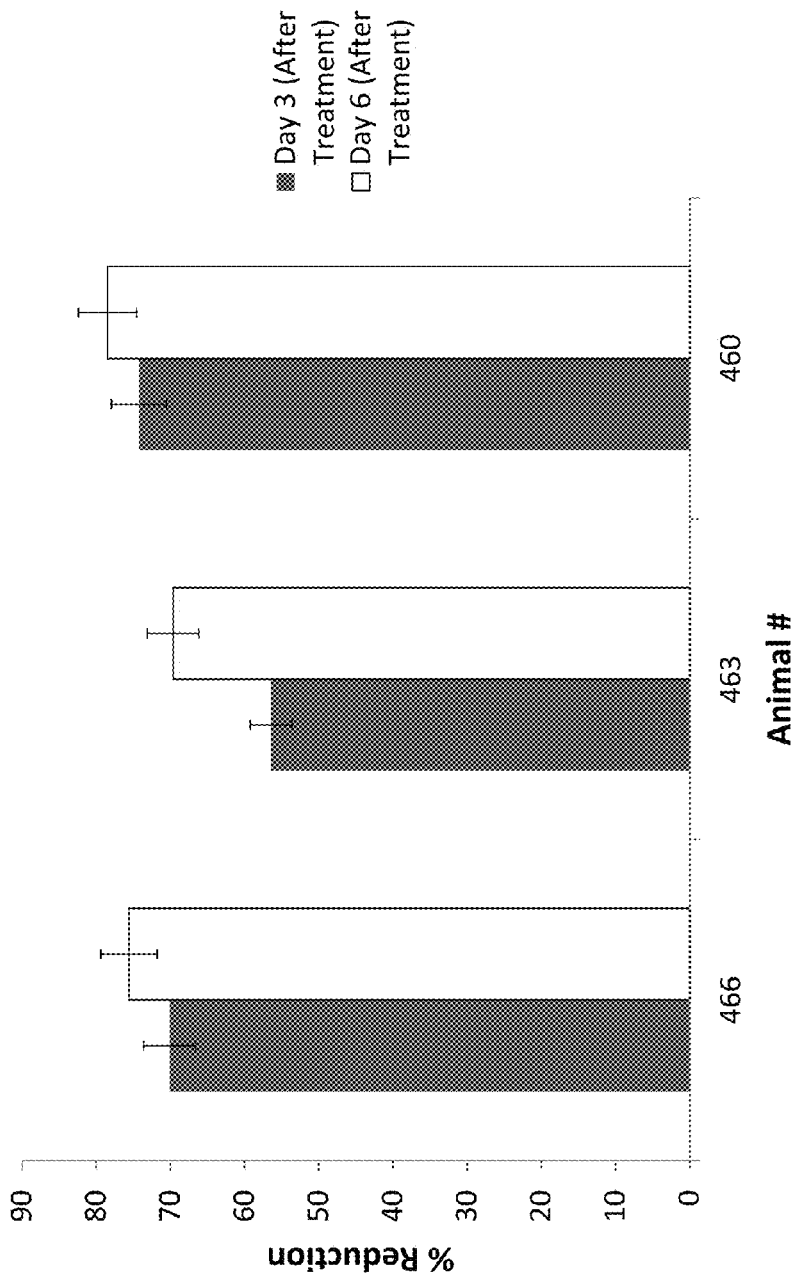

FIGS. 10A and 10B depict the effects of KB-2115 with Glycyrrhetinic acid (GA) on mice in terms of total cholesterol (FIG. 10A) and percent reduction in total cholesterol (FIG. 10B), in accordance with embodiments of the present invention.

Figure 11A:
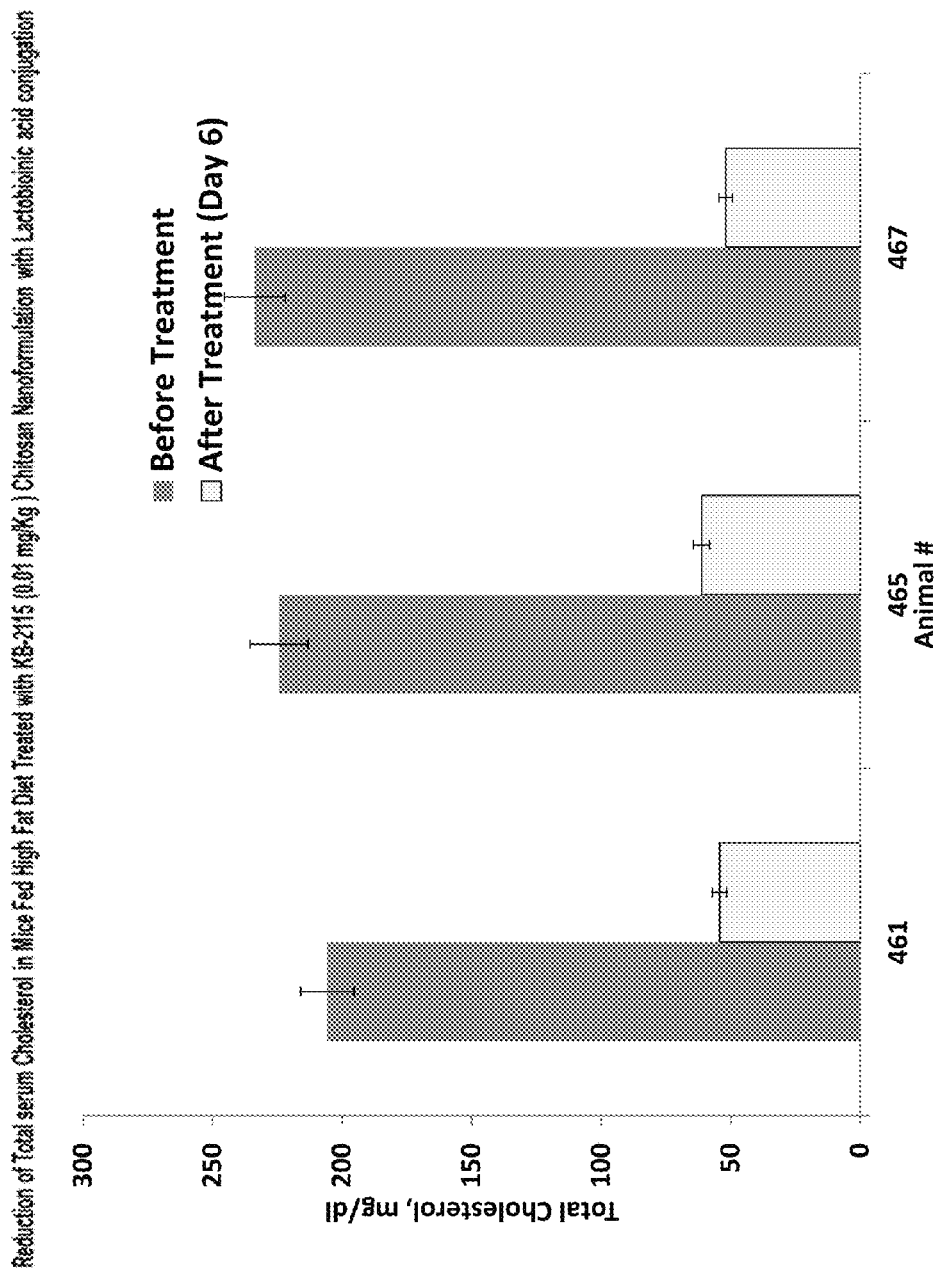
FIGS. 11A and 11B depict the effects of KB-2115, (0.01 mg/kg, daily for 6 days), encapsulated into Chitosan hybrid NP targeted with Lactobionic Acid (LA) on serum total cholesterol in mice fed high fat diet (FIG. 11A) and percent reduction in total cholesterol (FIG. 11B), in accordance with embodiments of the present invention.
Figure 11B:
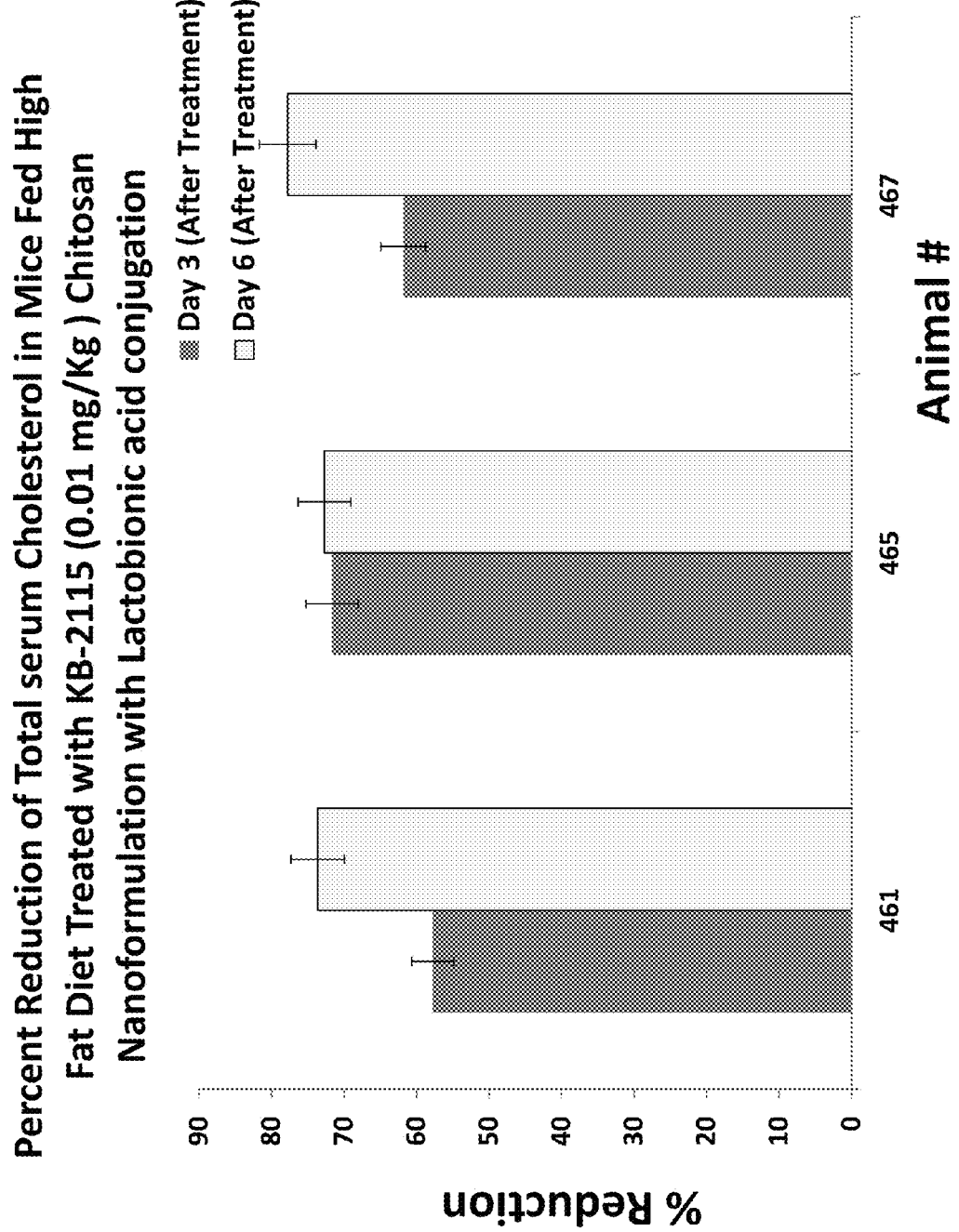

FIGS. 11A and 11B depict the effects of KB-2115 with Lactobionic Acid (LA) on mice in terms of total cholesterol (FIG. 11A) and percent reduction in total cholesterol (FIG. 11B), in accordance with embodiments of the present invention.

FIGS. 9A and 9B depict the effects of KB-2115 (0.1 mg/Kg, daily for 6 days) versus data shown in FIGS. 10A and 10B for KB-2115 (0.01 mg/Kg, daily for 6 days) encapsulated into Chitosan hybrid NPs conjugated with GA. Furthermore, data are shown in FIGS. 11A and 11B for KB-2115 (0.01 mg/Kg, daily for 6 days) encapsulated into Chitosan hybrid NPs conjugated with LA. Serum total cholesterol levels were reduced by 60-80% by KB-2115 at 0.1 mg/Kg daily for 6 days in high fat diet mice as shown in individually coded animals (FIGS. 9A and 9B). In contrast, KB-2115 chitosan fatty acid hybrid NPs targeted with either GA (FIGS. 10A and 10B) or LA (FIGS. 11A AND 11B) resulted in a similar reduction of serum cholesterol but at 10 fold lower doses.

Additionally, the effect on body weight gained due to high fat diet was examined and the data showed 10-20% body weight loss in the high fat diet animals after 6 days of daily treatment.

Figure 12:
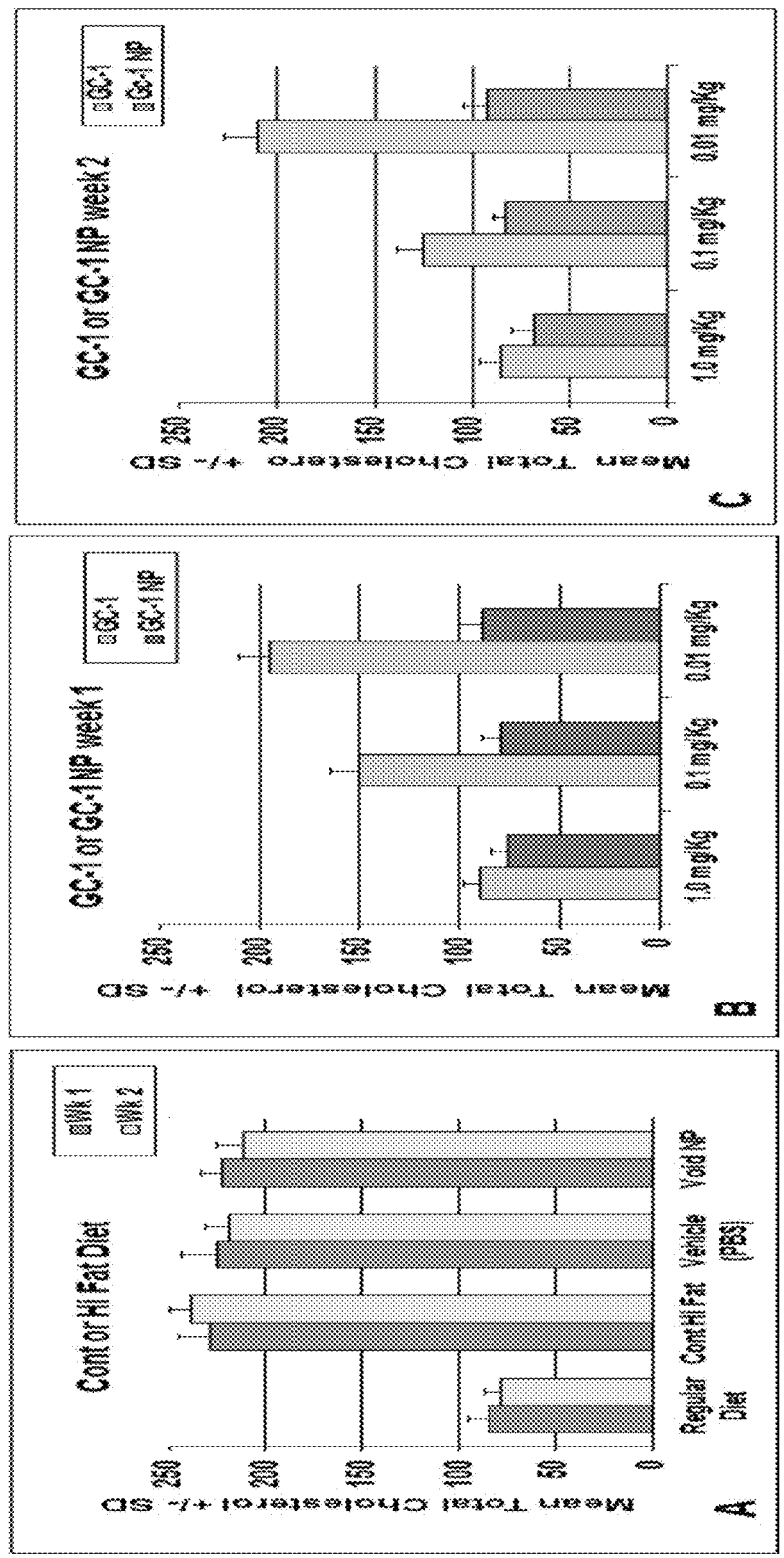
FIG. 12 depicts dose-ranging of Chitosan-PLGA NP-encapsulated GC-1 and conjugated with Glycyrrhetinic acid versus un-encapsulated GC-1 for lowering total cholesterol in mice fed high fat diet, in accordance with embodiments of the present invention.

Example 15: Nano-Hepatic Targeting with GC-1 and Impact of Serum Cholesterol in Mice High-fat diet (HFD)-induced dyslipidemia in mice. FIG. 12 depicts dose-ranging of Chitosan-PLGA NP-encapsulated GC-1 and conjugated with Glycyrrhetinic acid versus un-encapsulated GC-1 for lowering total cholesterol in HFD mice, in accordance with embodiments of the present invention. Panel A of FIG. 12 shows the Total Cholesterol values (mg/dl±SD in HFD-susceptible BL6 mouse strain with metabolic syndrome characterized by hypercholesterolemia, obesity, and diabetes. Regular Diet animals weigh 26±3; HF-diet animals weigh 46±5 grams. The total cholesterol in HFD animals is greater than 2 fold that of control animals. Values for NP vehicle (PBS) and void NP elicited no significant changes in total Cholesterol (FIG. 12, panel A).

Un-encapsulated (free) GC-1 showed a dose-dependent lowering of total cholesterol, with maximum effect toward the normal regular diet levels at 1.0 mg/kg administered IP daily to high fat diet fed mice. This lowering was observed both on week 1 (FIG. 12, panel B) and week 2 (FIG. 12, panel C). However, NP-encapsulated GC-1 significantly lowered total cholesterol at all 3 doses tested, showing a relatively flat dose-response. Importantly, the NP-encapsulated-GC-1 was highly effective at 10 and 100 fold lower doses than free GC-1. These data demonstrate the efficacy of NP encapsulated GC-1 and the fact that cholesterol lowering was accomplished at significantly lower doses in one of the NP formulations of the present invention. Recent studies in a laboratory of the inventor of the present invention showed increased differential liver uptake of GC-1 encapsulated into chitosan NPs (C-NP) conjugated with Glycyrrhetinic acid (GA) by 50 fold as compared to un-encapsulated GC-1 as measured by established LC/MS/MS method. Furthermore, C-NP conjugated with GA or Lactobionic acid administered in mice fed high fat diet lowered LDL-C to normal ranges with 10-100 folds lower doses as compared to GC-1.

Example 16: Solid Lipid NPs (SLN) Significantly Improved Hepatic Targeting of GC-1

Data demonstrated that the uptake of TR beta1 agonist (GC-1) encapsulated in SLN-NPs was evaluated in HepG2 cells versus other cells by confocal imaging where significant uptake was seen only in hepatic cells. SLN encapsulation and targeted with GA or LA resulted in a liver-specific greater than 10-fold increase in uptake. Hence encapsulation of TRβ agonists in either chitosan-PLGA or SLN NPs resulted in optimum hepatic delivery of drug, minimal systemic exposure, and significant efficacy in total cholesterol and LDL-C lowering. Hence, the effects of GC-1 SLN NPs conjugated with GA at 0.01 mg/kg daily for 3 weeks on serum cholesterol versus GC-SLN NP but without targeting with GA were examined (see FIG. 13). The data demonstrated comparable lowering of serum total cholesterol in HFD mice back to the regular diet levels with GC-1 SLN NP administered at 0.1 mg/Kg daily for 3 weeks, with similar results with GC-SLN NPs conjugated with GA but at 10 folds lower doses (0.01 mg/Kg, daily for 3 weeks).

Figure 13:
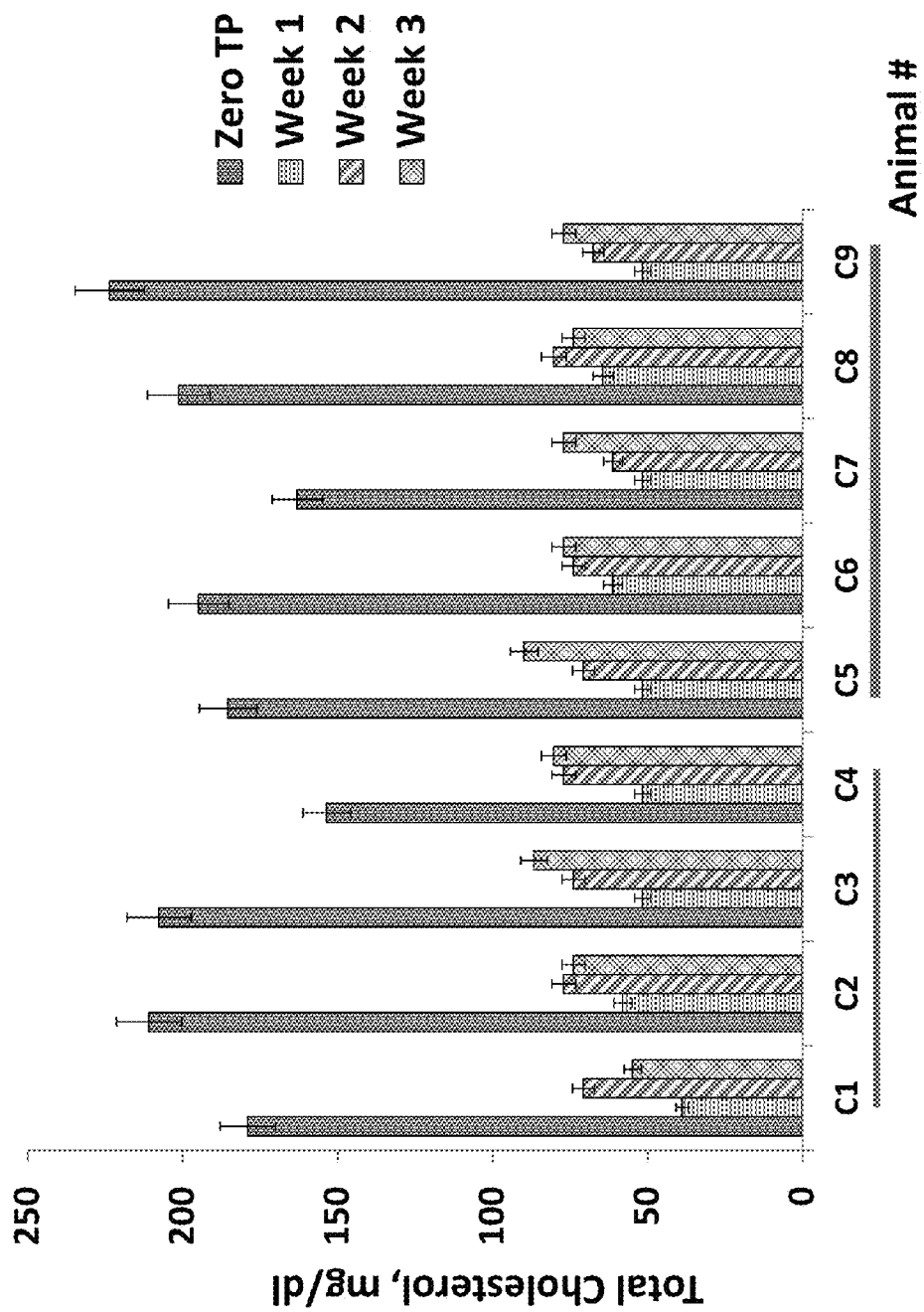
FIG. 13 illustrates the effect of un-encapsulated GC-1 at 0.1 mg/kg, daily for 3 weeks (HFD mice C1-C4) versus GC-1 encapsulated into Solid Lipid Nanoparticles (SLN-NP) conjugated with GA at 0.01 mg/kg, daily for 3 weeks (HFD mice C5-C9) on total serum cholesterol, in accordance with embodiments of the present invention.

FIG. 13 illustrates the effect, of GC-1 SLN NPs (0.1 mg/Kg) on animals C1-C4 versus GC-1 SLN NPs-GA (0.01 mg/kg) on animals C5-C9, on total cholesterol in high fat diet mice after three weeks of daily treatment, in accordance with embodiments of the present invention.

The composition of the present invention, which facilitates hepatic targeted delivery of thyroid receptor beta1 (TRβ1) agonist to a liver of a subject, comprises (i) hydrophobic nanoparticles; (ii) a liver targeting moiety exterior to each nanoparticle and covalently bonded to each nanoparticle; and (iii) at least one TRβ1 agonist encapsulated within each nanoparticle.

In one embodiment, the nanoparticles are selected from the group consisting of chitosan hybrid nanoparticles, amine-modified poly (lactic-co-glycolic acid) (PLGA) nanoparticles, and solid lipid nanoparticles, and combinations thereof.

In one embodiment, the liver targeting moiety is selected from the group consisting of Glycyrrhetinic acid (GA), Lactobionic acid (LA), and combinations thereof.

The composition of the present invention is illustrated in FIGS. 3 and 6, wherein the nanoparticles comprise: (i) an outer ring comprising the chitosan hybrid nanoparticles (FIG. 3), the solid lipid nanoparticles (FIG. 6), or the amine-modified PLGA (not explicitly shown in FIGS. 3 and 6); (ii) an interior portion which is surrounded by the outer ring and encapsulates at least one TRβ1 agonist; and (iii) a liver targeting moiety exterior to each nanoparticle and covalently bonded to each nanoparticle.

In one embodiment, the solid lipid nanoparticles comprise high density lipoprotein (HDL).

In one embodiment, the chitosan hybrid nanoparticles are selected from the group consisting of chitosan cross linked to fatty acids, chitosan cross linked to amino acids (e.g., arginine), chitosan cross linked to hyaluronic acid, chitosan cross linked to deoxycholic acid, chitosan cross linked to aliginic acids, chitosan cross linked to PLGA, and chitosan cross linked to collagen-hydroxyapatite.

In one embodiment, the fatty acids are selected from the group consisting of docosahexaenoic acid (DHA), eicosapentaenoic acid (EPA), DHA and EPA, and linoleic acid, and combinations thereof.

In one embodiment in addition to the at least one TRβ1 agonist, at least one other substance may be encapsulated within each nanoparticle, wherein the least one other substance is selected from the group consisting of statins, PCSK9 inhibitor, niacin, Peroxisome Proliferator-Activated Receptor Agonists (PPAR), and combinations thereof.

In one embodiment, the PPAR is selected from the group consisting of fibrates, Nicotinic acid, and combinations thereof.

In one embodiment, the at least one TRβ1 agonist is selected from the group consisting of Sobertirome (GC-1), Eprotirome (KB2115), and combinations thereof, or any other TRβ1 agonist known in the art.

In one embodiment, the at least one TRβ1 agonist comprises from 0.1 to 20.0% of a total weight of the composition.

In one embodiment, the present invention provides a method for targeted delivery of thyroid receptor beta1 (TRβ1) agonist to a liver of a subject. The subject may be a mammal, namely a human being or a non-human mammal. The method comprises administering the composition of the present invention to the subject.

In one embodiment, the composition is administered to the subject in an amount in a range of 0.001 to 1.0 mg per kilogram of body weight of the subject.

In one embodiment, the subject is a human subject having a disorder, wherein the administrating comprises administrating the composition to the subject in a therapeutically effect amount to treat the disorder, and wherein the disorder is selected from the group consisting of dyslipidemia, familial hypercholesterolemia, obesity, metabolic syndrome, type 2 diabetes, and combinations thereof. In one embodiment, the therapeutically effective amount of the composition is in a range of 0.001 to 1.0 mg per kilogram of body weight of the subject.

In one embodiment, the disorder comprises dyslipidemia and/or familial hypercholesterolemia, wherein the composition is administered to the subject in the therapeutically effective amount to lower serum cholesterol and/or triglyceride in the subject in order to reduce the subject's cardiovascular risk.

In one embodiment, the subject is obese, wherein the composition is administered to the subject in the therapeutically effective amount in order to reduce the body weight of the subject.

While particular embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A composition for hepatic targeted delivery of thyroid receptor beta1 (TRβ1) agonist to a liver of a subject, said composition comprising:
   hydrophobic nanoparticles, wherein the nanoparticles are selected from the group consisting of chitosan hybrid nanoparticles, amine-modified poly (lactic-co-glycolic acid) (PLGA) nanoparticles, solid lipid nanoparticles, and combinations thereof;
   a liver targeting moiety exterior to each nanoparticle and covalently bonded to each nanoparticle, said liver targeting moiety selected from the group consisting of Glycyrrhetinic acid (GA), Lactobionic acid (LA), and combinations thereof; and
   at least one TRβ1 agonist encapsulated within each nanoparticle, wherein a second dosage, reduced about ten fold from a first dosage, of the TRβ1 agonist in the composition exhibits about a two fold or more total cholesterol lowering in the subject as is exhibited by the first dosage of un-encapsulated TRβ1 agonist.

2. The composition of claim 1, wherein the nanoparticles comprise the solid lipid nanoparticles and the amine-modified PLGA nanoparticles.

3. The composition of claim 1, wherein the nanoparticles comprise the chitosan hybrid nanoparticles, and wherein the chitosan hybrid nanoparticles are selected from the group consisting of chitosan cross linked to fatty acids, chitosan cross linked to amino acids, chitosan cross linked to hyaluronic acid, chitosan cross linked to deoxycholic acid, chitosan cross linked to aliginic acids, chitosan cross linked to PLGA, and chitosan cross linked to collagen-hydroxyapatite.

4. The composition of claim 3, wherein the nanoparticles comprise the chitosan cross linked to fatty acids, and wherein the fatty acids are selected from the group consisting of docosahexaenoic acid (DHA), eicosapentaenoic acid (EPA), DHA and EPA, and linoleic acid, and combinations thereof.

5. The composition of claim 3, wherein the nanoparticles comprise the chitosan cross linked to collagen-hydroxyapatite.

6. The composition of claim 1, further comprising at least one other substance encapsulated within each nanoparticle, and wherein the least one other substance is selected from the group consisting of statins, PCSK9 inhibitor, niacin, Peroxisome Proliferator-Activated Receptor Agonists (PPAR), and combinations thereof.

7. The composition of claim 1, wherein the at least one TRβ1 agonist consists of Sobertirome (GC-1) and Eprotirome (KB2115).

8. A method for targeted delivery of thyroid receptor beta1 (TRβ1) agonist to a liver of a subject, said method comprising administering the composition of claim 1 to the subject.

9. The method of claim 8, wherein said administrating comprises administrating the composition to the subject in an amount in a range of 0.001 to 1.0 mg per kilogram of body weight of the subject.

10. The method of claim 8, wherein the subject is a human subject having a disorder, wherein said administrating comprises administrating the composition to the subject in a therapeutically effective amount to treat the disorder, and wherein the disorder is selected from the group consisting of dyslipidemia, familial hypercholesterolemia, obesity, metabolic syndrome, type 2 diabetes, and combinations thereof.

11. The method of claim 10, wherein the therapeutically effective amount of the composition is in a range of 0.001 to 1.0 mg per kilogram of body weight of the subject.

12. The method of claim 10, wherein the disorder comprises dyslipidemia and/or familial hypercholesterolemia, and wherein said administrating comprises administrating the composition to the subject in the therapeutically effective amount to lower serum cholesterol and/or triglyceride in the subject in order to reduce the subject's cardiovascular risk.

13. The method of claim 10, wherein the subject is obese, and wherein said administrating comprises administrating the composition to the subject in the therapeutically effective amount in order to reduce the body weight of the subject.

14. The composition of claim 1, wherein the nanoparticles comprise the chitosan hybrid nanoparticles and the solid lipid nanoparticles.

15. The composition of claim 14, wherein the solid lipid nanoparticles comprise high density lipoprotein (HDL).

16. The composition of claim 1, wherein the nanoparticles comprise the chitosan hybrid nanoparticles and the amine-modified PLGA.

17. The composition of claim 1, wherein the targeting moiety consists of (i) the Glycyrrhetinic acid (GA) exterior to each nanoparticle and covalently bonded to each nanoparticle and (ii) the Lactobionic acid (LA) exterior to each nanoparticle and covalently bonded to each nanoparticle.

18. The composition of claim 6, wherein the at least one other substance encapsulated within each nanoparticle comprises the PCSK9 inhibitor and the PPAR, and wherein the PPAR is selected from the group consisting of fibrates, Nicotinic acid, and combinations thereof.

19. The composition of claim 6, wherein the at least one other substance encapsulated within each nanoparticle comprises the PCSK9 inhibitor, the statins, and the niacin.

20. The composition of claim 3, wherein the nanoparticles comprise the chitosan cross linked to PLGA.

* * * * *